United States Patent
Weiner et al.

(10) Patent No.: US 11,851,477 B2
(45) Date of Patent: Dec. 26, 2023

(54) DNA MONOCLONAL ANTIBODIES TARGETING INFLUENZA VIRUS

(71) Applicants: David B. Weiner, Merion, PA (US); Ami Patel, Philadelphia, PA (US); Jian Yan, Wallingford, PA (US); Sarah Elliott, Pullman, WA (US)

(72) Inventors: David B. Weiner, Merion, PA (US); Ami Patel, Philadelphia, PA (US); Jian Yan, Wallingford, PA (US); Sarah Elliott, Pullman, WA (US)

(73) Assignees: The Trustees of the University of Pennsylvania, Philadelphia, PA (US); The Wistar Institute of Anatomy and Biology, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 1257 days.

(21) Appl. No.: 16/098,921

(22) PCT Filed: May 5, 2017

(86) PCT No.: PCT/US2017/031213
§ 371 (c)(1),
(2) Date: Nov. 5, 2018

(87) PCT Pub. No.: WO2017/192946
PCT Pub. Date: Nov. 9, 2017

(65) Prior Publication Data
US 2019/0135899 A1 May 9, 2019

Related U.S. Application Data

(60) Provisional application No. 62/376,162, filed on Aug. 17, 2016, provisional application No. 62/332,381, filed on May 5, 2016.

(51) Int. Cl.
| | | |
|---|---|---|
| C07K 16/28 | (2006.01) | |
| C07K 16/10 | (2006.01) | |
| A61P 31/16 | (2006.01) | |
| C12Q 1/68 | (2018.01) | |
| A61K 39/00 | (2006.01) | |
| C07K 16/24 | (2006.01) | |

(52) U.S. Cl.
CPC .......... *C07K 16/1018* (2013.01); *A61P 31/16* (2018.01); *A61K 2039/505* (2013.01); *A61K 2039/545* (2013.01); *C07K 16/248* (2013.01); *C07K 16/2866* (2013.01); *C07K 2317/76* (2013.01)

(58) Field of Classification Search
None
See application file for complete search history.

(56) References Cited

U.S. PATENT DOCUMENTS

2014/0331366 A1 11/2014 Yusibov
2015/0284448 A1 10/2015 Weiner

FOREIGN PATENT DOCUMENTS

| WO | 2013114885 A1 | 8/2013 |
| WO | 2015089492 | 6/2015 |
| WO | 2017165460 | 9/2017 |

OTHER PUBLICATIONS

Krause JC et al., "A Broadly Neutralizing Human Monoclonal Antibody that Recognizes a Conserved, Novel Epitope on the Globular Head of the Influenza H1N1 Virus Hemagglutinin", J. Virology, 2011, 85:10905-10908.
Supplementary Partial European Search Report dated Feb. 13, 2020, 16 pages.
Corti D et al., "A Neutralizing Antibody Selected from Plasma Cells That Binds to Group 1 and Group 2 Influenza A Hemagglutinins", Science, 2011, 333:850-856.
Flingai S et al., "Protection against dengue disease by synthetic nucleic acid antibody prophylaxis/immunotherapy", Scientific Reports, 2015, 5:12616, 9 pages.
Muthumani K et al., "Rapid and Long-Term Immunity Elicited by DNA-Encoded Antibody Prophylaxis and DNA Vaccination Against Chikungunya Virus", J Infectious Diseases, 2016, 214:369-378.
Pappas L et al., "Rapid development of broadly influenza neutralizing antibodies through redundant mutations", Nature, 2014, 516:418-422.
Elliot STC et al., "Abstract 433. DNA Monoclonal Antibodies Target Influenza Vi rus In Vivo", Molecular Therapy—Supplement 1, 2016, SI71-S172.
The American Society of Gene and Cell Therapy, "American Society of Gene & Cell Therapy 19th Annual Meeting—May 4-7, 2016 Washington. DC", Scientific Symposium, 2016, 24:i-xiv.
Elliott STC et al., "DMAb inoculation of synthetic cross reactive antibodies protects against lethal influenza A and B infections", NPJ Vaccines, 2017, 2:XP055661090, 9 pages.
International Search Report for PCT/US17/31213 dated Sep. 28, 2017, 5 pages.
Written Opinion of the International Searching Authority for PCT/US17/31213 dated Sep. 28, 2017, 7 pages.
International Preliminary Report on Patentability for PCT/US17/31213 dated Sep. 28, 2017, 8 pages.
Muthumani K et al., "Optimized and Enhanced DNA Plasmid Vector Based in Vivo Construction of a Neutralizing anti-HIV-1 Envelope Glycoprotein Fab", Hum. Vaccin. Immunother., 2013, 9:2253-2262.
Kallewaard NL et al., "Structure and Function Analysis of an Antibody Recognizing All Influenza A Subtypes", Cell, 2016, 166:596-608.

(Continued)

*Primary Examiner* — Sean McGarry
(74) *Attorney, Agent, or Firm* — Riverside Law LLP

(57) ABSTRACT

Disclosed herein is a composition including a recombinant nucleic acid sequence that encodes an anti-influenza-hemagglutinin synthetic antibody. The disclosure also provides a method of preventing and/or treating influenza in a subject using said composition and method of generation.

16 Claims, 24 Drawing Sheets

Specification includes a Sequence Listing.

(56) References Cited

OTHER PUBLICATIONS

Traggiai E et al., "An Efficient Method to Make Human Monoclonal Antibodies From Memory B Cells: Potent Neutralization of SARS Coronavirus", 2004, Nat Med 10:871-875.

Benjamin E et al., "A Broadly Neutralizing Human Monoclonal Antibody Directed against a Novel Conserved Epitope on the Influenza Virus H3 Hemagglutinin Globular Head", J. Virol., 2014, 88:6743-6750.

DMAb construct 5J8

Influenza DMAb contain variable regions from published anti-influenza monoclonal antibodies

5J8 (Krause et al, J Virol, 2011)
- Binds to receptor binding pocket on variable globular head
- Cross-reactive to multiple influenza-A H1 viruses

Influenza Hemagglutinin

Figure 1

SEQUENCE LISTING

```
<160> NUMBER OF SEQ ID NOS: 16

<210> SEQ ID NO 1
<211> LENGTH: 735
<212> TYPE: PRT
<213> ORGANISM: Artificial Sequence
<220> FEATURE:
<223> OTHER INFORMATION: pGX9211

<400> SEQUENCE: 1

Met Asp Trp Thr Trp Arg Ile Leu Phe Leu Val Ala Ala Ala Thr Gly
1               5                   10                  15

Thr His Ala Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Asn Asn Ala Val Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Glu Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Ser Gly His Ile Thr Val Phe Gly
        115                 120                 125

Val Asn Val Asp Ala Phe Asp Met Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
```

```
                      165                 170                 175
Lys Asp Tyr Phe Pro Glu Pro Val Thr Val Ser Trp Asn Ser Gly Ala
                180                 185                 190

Leu Thr Ser Gly Val His Thr Phe Pro Ala Val Leu Gln Ser Ser Gly
            195                 200                 205

Leu Tyr Ser Leu Ser Ser Val Val Thr Val Pro Ser Ser Ser Leu Gly
        210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Arg Gly Arg
465                 470                 475                 480

Lys Arg Arg Ser Gly Ser Gly Ala Thr Asn Phe Ser Leu Leu Lys Gln
                485                 490                 495

Ala Gly Asp Val Glu Glu Asn Pro Gly Pro Met Val Leu Gln Thr Gln
            500                 505                 510

Val Phe Ile Ser Leu Leu Leu Trp Ile Ser Gly Ala Tyr Gly Asp Ile
        515                 520                 525

Gln Met Thr Gln Ser Pro Ser Ser Leu Ser Ala Ser Val Gly Asp Arg
    530                 535                 540

Val Thr Ile Thr Cys Arg Thr Ser Gln Ser Leu Ser Ser Tyr Leu His
545                 550                 555                 560

Trp Tyr Gln Gln Lys Pro Gly Lys Ala Pro Lys Leu Leu Ile Tyr Ala
                565                 570                 575

Ala Ser Ser Leu Gln Ser Gly Val Pro Ser Arg Phe Ser Gly Ser Gly
            580                 585                 590
```

```
Ser Gly Thr Asp Phe Thr Leu Thr Ile Ser Ser Leu Gln Pro Glu Asp
            595                 600                 605

Phe Ala Thr Tyr Tyr Cys Gln Gln Ser Arg Thr Phe Gly Gln Gly Thr
        610                 615                 620

Lys Val Glu Ile Lys Thr Val Ala Ala Pro Ser Val Phe Ile Phe Pro
625                 630                 635                 640

Pro Ser Asp Glu Gln Leu Lys Ser Gly Thr Ala Ser Val Val Cys Leu
                645                 650                 655

Leu Asn Asn Phe Tyr Pro Arg Glu Ala Lys Val Gln Trp Lys Val Asp
            660                 665                 670

Asn Ala Leu Gln Ser Gly Asn Ser Gln Glu Ser Val Thr Glu Gln Asp
        675                 680                 685

Ser Lys Asp Ser Thr Tyr Ser Leu Ser Asn Thr Leu Thr Leu Ser Lys
    690                 695                 700

Ala Asp Tyr Glu Lys His Lys Val Tyr Ala Cys Glu Val Thr His Gln
705                 710                 715                 720

Gly Leu Ser Ser Pro Val Thr Lys Ser Phe Asn Arg Gly Glu Cys
                725                 730                 735

<210> SEQ ID NO 2
<211> LENGTH: 745
<212> TYPE: PRT
<213> ORGANISM: Artificial Sequence
<220> FEATURE:
<223> OTHER INFORMATION: pGX9212

<400> SEQUENCE: 2

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Lys
            20                  25                  30

Pro Gly Gly Ser Leu Arg Leu Ser Cys Ala Ala Ser Gly Leu Thr Phe
        35                  40                  45

Leu Asn Ala Trp Met Ser Trp Val Arg Gln Ala Pro Gly Lys Gly Leu
    50                  55                  60

Glu Trp Val Gly Arg Ile Lys Ser Asn Thr Asp Gly Gly Thr Thr Asp
65                  70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Ser Ser Leu Lys Thr Glu Asp Thr
            100                 105                 110

Ala Val Tyr Tyr Cys Thr Thr Asp Gly Pro Tyr Ser Asp Asp Phe Arg
        115                 120                 125

Ser Gly Tyr Ala Ala Arg Tyr Arg Tyr Phe Gly Met Asp Val Trp Gly
    130                 135                 140

Gln Gly Thr Thr Val Thr Val Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220
```

-continued

```
Pro Ser Ser Ser Leu Gly Thr Gln Thr Tyr Ile Cys Asn Val Asn His
225                 230                 235                 240

Lys Pro Ser Asn Thr Lys Val Asp Lys Lys Val Glu Pro Lys Ser Cys
            245                 250                 255

Asp Lys Thr His Thr Cys Pro Pro Cys Pro Ala Pro Glu Leu Leu Gly
        260                 265                 270

Gly Pro Ser Val Phe Leu Phe Pro Pro Lys Pro Lys Asp Thr Leu Met
    275                 280                 285

Ile Ser Arg Thr Pro Glu Val Thr Cys Val Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
            325                 330                 335

Arg Val Val Ser Val Leu Thr Val Leu His Gln Asp Trp Leu Asn Gly
        340                 345                 350

Lys Glu Tyr Lys Cys Lys Val Ser Asn Lys Ala Leu Pro Ala Pro Ile
    355                 360                 365

Glu Lys Thr Ile Ser Lys Ala Lys Gly Gln Pro Arg Glu Pro Gln Val
370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
        420                 425                 430

Val Leu Asp Ser Asp Gly Ser Phe Phe Leu Tyr Ser Lys Leu Thr Val
    435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Arg Gly Arg Lys Arg Arg Ser Gly Ser Gly Ala Thr Asn
            485                 490                 495

Phe Ser Leu Leu Lys Gln Ala Gly Asp Val Glu Glu Asn Pro Gly Pro
        500                 505                 510

Met Val Leu Gln Thr Gln Val Phe Ile Ser Leu Leu Leu Trp Ile Ser
    515                 520                 525

Gly Ala Tyr Gly Asp Ile Gln Met Thr Gln Ser Pro Ser Ser Val Ser
530                 535                 540

Ala Ser Val Gly Asp Arg Val Thr Ile Thr Cys Arg Ala Ser Gln Asp
545                 550                 555                 560

Ile Ser Thr Trp Leu Ala Trp Tyr Gln Gln Lys Pro Gly Lys Ala Pro
            565                 570                 575

Lys Leu Leu Ile Tyr Ala Ala Ser Ser Leu Gln Ser Gly Val Pro Ser
        580                 585                 590

Arg Phe Ser Gly Ser Gly Ser Gly Thr Asp Phe Thr Leu Thr Ile Ser
    595                 600                 605

Ser Leu Gln Pro Glu Asp Phe Ala Thr Tyr Tyr Cys Gln Gln Ala Asn
    610                 615                 620

Ser Phe Pro Pro Thr Phe Gly Gln Gly Thr Lys Leu Glu Ile Lys Thr
625                 630                 635                 640
```

-continued

```
Val Ala Ala Pro Ser Val Phe Ile Phe Pro Pro Ser Asp Glu Gln Leu
                645                 650                 655

Lys Ser Gly Thr Ala Ser Val Val Cys Leu Leu Asn Asn Phe Tyr Pro
            660                 665                 670

Arg Glu Ala Lys Val Gln Trp Lys Val Asp Asn Ala Leu Gln Ser Gly
        675                 680                 685

Asn Ser Gln Glu Ser Val Thr Glu Gln Asp Ser Lys Asp Ser Thr Tyr
    690                 695                 700

Ser Leu Ser Asn Thr Leu Thr Leu Ser Lys Ala Asp Tyr Glu Lys His
705                 710                 715                 720

Lys Val Tyr Ala Cys Glu Val Thr His Gln Gly Leu Ser Ser Pro Val
                725                 730                 735

Thr Lys Ser Phe Asn Arg Gly Glu Cys
                740                 745

<210> SEQ ID NO 3
<211> LENGTH: 736
<212> TYPE: PRT
<213> ORGANISM: Artificial Sequence
<220> FEATURE:
<223> OTHER INFORMATION: pGX222hc

<400> SEQUENCE: 3

Met Asp Trp Thr Trp Arg Ile Leu Phe Leu Val Ala Ala Thr Gly
1               5                   10                  15

Thr His Ala Glu Val Gln Leu Val Glu Ser Gly Pro Gly Leu Val Lys
            20                  25                  30

Pro Ser Asp Ile Leu Ser Leu Thr Cys Ala Val Ser Gly Tyr Ser Ile
        35                  40                  45

Ser Ser Asn Tyr Tyr Trp Gly Trp Ile Arg Gln Pro Pro Gly Lys Gly
    50                  55                  60

Leu Glu Trp Ile Gly Ser Ile Tyr His Ser Gly Ser Thr Tyr Tyr Lys
65                  70                  75                  80

Pro Ser Leu Glu Ser Arg Leu Gly Ile Ser Val Asp Thr Ser Lys Asn
                85                  90                  95

Gln Phe Ser Leu Lys Leu Ser Phe Val Ser Ala Ala Asp Thr Ala Val
            100                 105                 110

Tyr Tyr Cys Ala Arg His Val Arg Ser Gly Tyr Pro Asp Thr Ala Tyr
        115                 120                 125

Tyr Phe Asp Lys Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255
```

```
Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Val Leu Gln Thr Gln Val Phe Ile Ser
            500                 505                 510

Leu Leu Leu Trp Ile Ser Gly Ala Tyr Gly Ser Tyr Val Leu Thr Gln
        515                 520                 525

Pro Pro Ser Val Ser Val Ala Pro Gly Glu Thr Ala Arg Ile Ser Cys
    530                 535                 540

Gly Gly Asn Asn Ile Gly Thr Lys Val Leu His Trp Tyr Gln Gln Thr
545                 550                 555                 560

Pro Gly Gln Ala Pro Val Leu Val Val Tyr Asp Asp Ser Asp Arg Pro
                565                 570                 575

Ser Gly Ile Pro Glu Arg Phe Ser Gly Ser Asn Ser Gly Asn Thr Ala
            580                 585                 590

Thr Leu Thr Ile Ser Arg Val Glu Val Gly Asp Glu Ala Asp Tyr Tyr
        595                 600                 605

Cys Gln Val Trp Asp Ile Ser Thr Asp Gln Ala Val Phe Gly Gly Gly
    610                 615                 620

Thr Lys Leu Thr Val Leu Gly Gln Pro Lys Ala Ala Pro Ser Val Thr
625                 630                 635                 640

Leu Phe Pro Pro Ser Ser Glu Glu Leu Gln Ala Asn Lys Ala Thr Leu
                645                 650                 655

Val Cys Leu Ile Ser Asp Phe Tyr Pro Gly Ala Val Thr Val Ala Trp
            660                 665                 670

Lys Ala Asp Ser Ser Pro Val Lys Ala Gly Val Glu Thr Thr Thr Pro
```

```
            675                 680                 685
Ser Lys Gln Ser Asn Asn Lys Tyr Ala Ala Ser Ser Tyr Leu Ser Leu
        690                 695                 700

Thr Pro Glu Gln Trp Lys Ser His Arg Ser Tyr Ser Cys Gln Val Thr
705                 710                 715                 720

His Glu Gly Ser Thr Val Glu Lys Thr Val Ala Pro Thr Glu Cys Ser
                    725                 730                 735

<210> SEQ ID NO 4
<211> LENGTH: 744
<212> TYPE: PRT
<213> ORGANISM: Artificial Sequence
<220> FEATURE:
<223> OTHER INFORMATION: pGX2221c

<400> SEQUENCE: 4

Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Thr Tyr Ala Met His Trp Val Arg Gln Ala Pro Gly Lys Gly Leu
    50                  55                  60

Glu Trp Val Ala Val Ile Ser Tyr Asp Ala Asn Tyr Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Ser Gln Leu Arg Ser Leu Leu Tyr Phe Glu
        115                 120                 125

Trp Leu Ser Gln Gly Tyr Phe Asp Tyr Trp Gly Gln Gly Thr Leu Val
    130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Ile Cys Asn Val Asn His Lys Pro Ser Asn Thr
225                 230                 235                 240

Lys Val Asp Lys Lys Val Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
```

```
                305                 310                 315                 320
Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys Arg Gly
465                 470                 475                 480

Arg Lys Arg Arg Ser Gly Ser Gly Ala Thr Asn Phe Ser Leu Leu Lys
                485                 490                 495

Gln Ala Gly Asp Val Glu Glu Asn Pro Gly Pro Met Val Leu Gln Thr
            500                 505                 510

Gln Val Phe Ile Ser Leu Leu Leu Trp Ile Ser Gly Ala Tyr Gly Asp
            515                 520                 525

Ile Val Met Thr Gln Ser Pro Asp Ser Leu Ala Val Ser Leu Gly Glu
            530                 535                 540

Arg Ala Thr Ile Asn Cys Lys Ser Ser Gln Ser Val Thr Phe Asn Tyr
545                 550                 555                 560

Lys Asn Tyr Leu Ala Trp Tyr Gln Gln Lys Pro Gly Gln Pro Pro Lys
                565                 570                 575

Leu Leu Ile Tyr Trp Ala Ser Thr Arg Glu Ser Gly Val Pro Asp Arg
            580                 585                 590

Phe Ser Gly Ser Gly Ser Gly Thr Asp Phe Thr Leu Thr Ile Ser Ser
        595                 600                 605

Leu Gln Ala Glu Asp Val Ala Val Tyr Tyr Cys Gln Gln His Tyr Arg
    610                 615                 620

Thr Pro Pro Thr Phe Gly Gln Gly Thr Lys Val Glu Ile Lys Thr Val
625                 630                 635                 640

Ala Ala Pro Ser Val Phe Ile Phe Pro Pro Ser Asp Glu Gln Leu Lys
                645                 650                 655

Ser Gly Thr Ala Ser Val Val Cys Leu Leu Asn Asn Phe Tyr Pro Arg
            660                 665                 670

Glu Ala Lys Val Gln Trp Lys Val Asp Asn Ala Leu Gln Ser Gly Asn
            675                 680                 685

Ser Gln Glu Ser Val Thr Glu Gln Asp Ser Lys Asp Ser Thr Tyr Ser
    690                 695                 700

Leu Ser Asn Thr Leu Thr Leu Ser Lys Ala Asp Tyr Glu Lys His Lys
705                 710                 715                 720

Val Tyr Ala Cys Glu Val Thr His Gln Gly Leu Ser Ser Pro Val Thr
                725                 730                 735
```

```
Lys Ser Phe Asn Arg Gly Glu Cys
                740

<210> SEQ ID NO 5
<211> LENGTH: 477
<212> TYPE: PRT
<213> ORGANISM: Artificial Sequence
<220> FEATURE:
<223> OTHER INFORMATION: pGX9223

<400> SEQUENCE: 5

Met Asp Trp Thr Trp Arg Ile Leu Phe Leu Val Ala Ala Ala Thr Gly
1               5                   10                  15

Thr His Ala Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Asn Asn Ala Val Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Glu Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Ser Gly His Ile Thr Val Phe Gly
        115                 120                 125

Val Asn Val Asp Ala Phe Asp Met Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350
```

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
        370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
450                 455                 460

His Tyr Thr Gln Lys Ser Leu Ser Leu Ser Pro Gly Lys
465                 470                 475

<210> SEQ ID NO 6
<211> LENGTH: 229
<212> TYPE: PRT
<213> ORGANISM: Artificial Sequence
<220> FEATURE:
<223> OTHER INFORMATION: pGX9231

<400> SEQUENCE: 6

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Thr Ser Gln Ser
        35                  40                  45

Leu Ser Ser Tyr Leu His Trp Tyr Gln Gln Lys Pro Gly Lys Ala Pro
    50                  55                  60

Lys Leu Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Arg
            100                 105                 110

Thr Phe Gly Gln Gly Thr Lys Val Glu Ile Lys Thr Val Ala Ala Pro
        115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Asn
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 7
<211> LENGTH: 477
<212> TYPE: PRT
<213> ORGANISM: Artificial Sequence
<220> FEATURE:
<223> OTHER INFORMATION: pGX9310

<400> SEQUENCE: 7

```
Met Asp Trp Thr Trp Arg Ile Leu Phe Leu Val Ala Ala Ala Thr Gly
1               5                   10                  15

Thr His Ala Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Asn Asn Ala Val Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Glu Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Ser Gly His Ile Thr Val Phe Gly
        115                 120                 125

Val Asn Val Asp Ala Phe Asp Met Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365
```

```
Ala Lys Gly Gln Pro Arg Glu Pro Gln Val Tyr Thr Leu Pro Pro Ser
        370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 8
<211> LENGTH: 229
<212> TYPE: PRT
<213> ORGANISM: Artificial Sequence
<220> FEATURE:
<223> OTHER INFORMATION: pGX9311

<400> SEQUENCE: 8

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Thr Ser Gln Ser
        35                  40                  45

Leu Ser Tyr Leu His Trp Tyr Gln Gln Lys Pro Gly Lys Ala Pro
    50                  55                  60

Lys Leu Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Arg
            100                 105                 110

Thr Phe Gly Gln Gly Thr Lys Val Glu Ile Lys Thr Val Ala Ala Pro
        115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Asn
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 9
```

<211> LENGTH: 2211
<212> TYPE: DNA
<213> ORGANISM: Artificial Sequence
<220> FEATURE:
<223> OTHER INFORMATION: pGX9211

<400> SEQUENCE: 9

| | | | | | |
|---|---|---|---|---|---|
| atggattgga | cttggaggat | tctgtttctg | gtcgccgccg | ctactggaac | tcacgctcag | 60 |
| gtgcagctgc | agcagtctgg | acccggactg | gtgaagcctt | cacagactct | gagcctgacc | 120 |
| tgcgccatct | ccggcgactc | tgtgagctcc | aacaatgctg | tctggaactg | gattagacag | 180 |
| tccccatctc | gggggctgga | atggctggga | cgaacatact | ataggagcaa | atggtacaat | 240 |
| gactatgctg | agagtgtgaa | gtcacgaatc | acaattaacc | cagatactag | caagaatcag | 300 |
| ttctcccctg | cagctgaactc | tgtgacaccc | gaggatactg | cagtctacta | ttgcgcacgc | 360 |
| tccggacaca | tcaccgtgtt | cggagtcaat | gtggacgcct | ttgatatgtg | gggacagggg | 420 |
| accacagtca | cagtgtctag | tgcaagtact | aaaggcccat | cagtgtttcc | cctggcccct | 480 |
| tcaagcaaga | gtacctcagg | cggaacagcc | gctctgggat | gtctggtgaa | ggactacttc | 540 |
| cctgagccag | tcaccgtgag | ctggaactcc | ggagctctga | ccagcggggt | gcatacattt | 600 |
| cctgcagtcc | tgcagtcctc | tggcctgtac | agcctgagtt | cagtggtcac | cgtgccaagc | 660 |
| tcctctctgg | gaacagagac | ttatatctgc | aacgtgaatc | acaaaccatc | caatacaaag | 720 |
| gtcgacaaga | agtggaacc | caaatcttgt | gataagaccc | atacatgccc | tccctgtcca | 780 |
| gcacctgagc | tgctgggcgg | cccatccgtg | ttcctgtttc | cacccaagcc | taaagacaca | 840 |
| ctgatgatta | gccggactcc | cgaagtgacc | tgcgtggtcg | tggacgtgag | ccacgaggac | 900 |
| cccgaagtga | agttcaactg | gtacgtggat | ggcgtcgagg | tgcataatgc | caagaccaaa | 960 |
| cctagggagg | aacagtacaa | cagcacttat | agagtcgtgt | ccgtcctgac | cgtgctgcac | 1020 |
| caggattggc | tgaacgggaa | ggagtataag | tgcaaagtgt | ccaacaaggc | cctgccagct | 1080 |
| cccatcgaga | agaccatttc | taaggccaaa | ggccagccac | gggaaccca | ggtgtacaca | 1140 |
| ctgcctccaa | gccgcgacga | gctgaccaaa | aaccaggtga | gcctgacatg | tctggtcaag | 1200 |
| ggattctatc | ctagtgatat | cgctgtggag | tgggaatcta | atgggcagcc | agaaaacaat | 1260 |
| tacaagacta | cccctcccgt | gctggactct | gatggaagtt | tctttctgta | ttcaaaactg | 1320 |
| accgtggaca | agagccgctg | gcagcagggg | aacgtcttta | gctgctccgt | gatgcacgag | 1380 |
| gccctgcaca | atcattacac | tcagaaatct | ctgagtctgt | cacccggaaa | acgaggacga | 1440 |
| aagaggagaa | gcggctccgg | agctaccaac | ttctcccctgc | tgaagcaggc | aggggatgtg | 1500 |
| gaggaaaatc | ctggcccaat | ggtcctgcag | acacaggtgt | ttatctctct | gctgctgtgg | 1560 |
| attagtggcg | cttacggaga | catccagatg | actcagtctc | ctagttcact | gtctgcaagt | 1620 |
| gtcggcgatc | gcgtgactat | tacctgtcga | acctcacaga | gcctgagctc | ctacctgcat | 1680 |
| tggtatcagc | agaagcctgg | gaaagcacca | agctgctga | tctatgcagc | ctctagtctg | 1740 |
| cagtccggcg | tgccctctag | gttctccggg | tctggcagtg | gaactgactt | tacactgact | 1800 |
| atttcaagcc | tgcagcctga | ggatttcgct | acctactatt | gccagcagag | cagaactttt | 1860 |
| gggcagggca | ccaaagtcga | aatcaagaca | gtggctgcac | catccgtctt | catttttcca | 1920 |
| ccctctgacg | agcagctgaa | gagtggaact | gcctcagtgg | tgtgcctgct | gaacaatttc | 1980 |
| tacccccggg | aagccaaagt | ccagtggaag | gtggataacg | ctctgcagtc | aggcaatagc | 2040 |
| caggagtccg | tgacagaaca | ggactctaaa | gatagtactt | attcactgag | caacaccctg | 2100 |
| acactgagca | aggcagacta | cgagaagcac | aaagtgtatg | cctgcgaagt | gacccaccag | 2160 | gggctgagca gtccagtgac caaatctttc aacaggggag aatgttgata a        2211

<210> SEQ ID NO 10
<211> LENGTH: 2241
<212> TYPE: DNA
<213> ORGANISM: Artificial Sequence
<220> FEATURE:
<223> OTHER INFORMATION: pGX9212

<400> SEQUENCE: 10

| | |
|---|---|
| atggactgga cttggaggat tctgtttctg gtggccgccg caactggcac tcatgccgag | 60 |
| gtgcagctgg tggaatcagg ggaggactg gtgaagcctg gcggatcact gcgactgagc | 120 |
| tgcgcagctt ccggactgac cttcctgaac gcttggatga ctgggtgcg acaggcacca | 180 |
| gggaaaggcc tggaatgggt cgggcgcatc aagagcaata cagacggcgg aaccacagat | 240 |
| tacgcagccc ccgtgaaagg caggttcacc atttctcggg acgatagtaa gaacacactg | 300 |
| tatctgcaga tgagctccct gaaaaccgag gacacagccg tgtactattg cactaccgat | 360 |
| ggcccctaca gcgacgattt ccgctccgga tatgctgcac ggtaccgcta ttttgggatg | 420 |
| gacgtgtggg gacaggggac aactgtcaca gtgtctagtg catctactaa ggacctagc | 480 |
| gtgttcccac tggcccccct caagcaaatca actagcggag ggaccgccgc tctgggatgt | 540 |
| ctggtgaagg attacttccc cgagcctgtc accgtgagct ggaactccgg ggccctgacc | 600 |
| tccggagtgc acacatttcc tgctgtcctg cagtcctctg ggctgtactc tctgagttca | 660 |
| gtggtcacag tgccaagctc ctctctgggc actcagacct atatctgcaa cgtgaatcac | 720 |
| aaacctagca atactaaggt cgacaagaaa gtggaaccaa aaagctgtga taagacacat | 780 |
| acttgcccctc cctgtccagc tccagagctg ctgggcggac catccgtgtt cctgttccca | 840 |
| cccaagccca agacacccct gatgatttcc cggacaccag aagtgacttg cgtggtcgtg | 900 |
| gacgtgagcc acgaggaccc cgaagtgaag ttcaactggt acgtggatgg cgtcgaggtg | 960 |
| cataatgcca agacaaaacc cagggaggaa cagtacaact caacttatag agtcgtgagc | 1020 |
| gtcctgaccg tgctgcacca ggactggctg aacggcaagg agtataagtg caaagtgagc | 1080 |
| aacaaggccc tgcctgctcc aatcgagaag actattagca aggctaaagg acagcctcgg | 1140 |
| gaaccacagg tgtacaccct gcctccatcc cgcgacgagc tgaccaaaaa ccaggtgtct | 1200 |
| ctgacatgtc tggtcaaggg cttctatccc tctgatatcg ccgtggagtg ggaaagtaat | 1260 |
| ggacagcctg aaaacaatta caagaccaca cccctgtgc tggactctga tggcagtttc | 1320 |
| tttctgtata gtaaactgac cgtggacaag tcaagatggc agcagggaaa cgtgtttttcc | 1380 |
| tgctctgtca tgcatgaggc cctgcacaat cattcaccc agaagagtct gtcactgagc | 1440 |
| ccaggaaaac gagggaggaa gaggagatcc ggctctggag ccacaaactt ctccctgctg | 1500 |
| aagcaggctg agacgtggga ggaaaatccc gggcctatgg tgctgcagac ccaggtcttt | 1560 |
| atctcctgc tgctgtggat ttctggcgct acggagata tccagatgac acagtctccc | 1620 |
| agttcagtca gtgcatcagt gggcgaccgc gtcaccatca catgtcgagc atcacaggat | 1680 |
| attagcacct ggctggcctg gtaccagcag aagcccggaa aagctcctaa gctgctgatc | 1740 |
| tatgcagcca gctccctgca gtccggagtg ccctctaggt tcagcgggtc cggctctgga | 1800 |
| acagacttta ctctgaccat ttctagtctg cagcctgagg atttcgcaac ttactattgc | 1860 |
| cagcaggcca acagcttccc acccactttt gggcagggcca ccaaactgga aatcaagact | 1920 |
| gtggctgcac ctagcgtctt cattttttcct ccatccgacg agcagctgaa gagtggcacc | 1980 |

```
gcctcagtgg tgtgcctgct gaacaacttc tacccaagag aagcaaaagt gcagtggaag    2040
gtcgataacg ccctgcagtc aggcaatagc caggagtccg tgacagaaca ggactctaag    2100
gatagtactt atagtctgtc aaatacactg actctgagca aagctgacta cgagaagcat    2160
aaagtgtatg catgcgaggt cactcaccag ggactgtctt cacccgtcac caaatctttc    2220
aatagaggag aatgctgata a                                              2241
```

<210> SEQ ID NO 11
<211> LENGTH: 2214
<212> TYPE: DNA
<213> ORGANISM: Artificial Sequence
<220> FEATURE:
<223> OTHER INFORMATION: pGX222hc

<400> SEQUENCE: 11

```
atggactgga catggagaat cctgttcctg gtcgccgccg ctactgggac tcacgcagaa      60
gtgcagctgg tcgaatcagg gcctgggctg gtgaagccct cagacatcct gagcctgacc     120
tgcgccgtgt ctggctacag tatcagctcc aactactatt ggggatggat tcggcagccc     180
cctggcaagg gactggaatg gatcgggtcc atctaccact caggcagcac ctactataaa     240
ccttcactgg agagccgcct gggaatttcc gtggacacat ctaagaatca gttcagcctg     300
aaactgtcct ttgtctctgc cgctgatact gcagtgtact attgcgcccg acatgtcagg     360
tccggctacc cagacaccgc ttactatttt gataagtggg gcagggcac cctggtcaca     420 gtgtctagtg ctagcaccaa gggcccctcc gtgttccctc tggcaccatc aagcaaatcc     480
acatctggcg gaactgcagc cctgggatgt ctggtgaagg attacttccc agagcccgtc     540
acagtgagtt ggaactcagg cgcactgact tctggagtcc acacctttcc cgccgtgctg     600
cagtcctctg gcctgtacag cctgagttca gtggtcacag tgcctagctc ctctctggga     660
actcagacct atatctgcaa cgtgaatcac aagccctcaa atactaaagt cgacaagaaa     720
gtggaaccta gtcttgtgaa taaacacat acttgcccac catgtcctgc accagagctg     780
ctgggaggac caagcgtgtt cctgtttcct ccaaagccca agacaccct gatgatctcc     840 agaacccctg aagtgacatg tgtggtcgtg gacgtctctc acgaggaccc cgaagtcaag     900
tttaactggt acgtggatgg cgtcgaggtg cataatgcta agacaaaacc ccgcgaggaa     960
cagtacaact caacctatcg agtcgtgagc gtcctgacag tgctgcacca ggactggctg    1020
aacggaaagg agtataagtg caaagtgagc aataaggcac tgcccgcccc tatcgagaaa    1080
actatttcca aggctaaagg gcagcccagg gaacctcagg tgtacaccct gccccttct    1140 agagacgagc tgacaaagaa ccaggtcagt ctgacttgtc tggtgaaagg attttatcca    1200
agtgatatcg cagtggagtg ggaatcaaat gggcagcccg aaaacaatta caagaccaca    1260
ccacccgtgc tggacagcga tggcagcttc ttcctgtatt ccaagctgac cgtggacaaa    1320
tctcggtggc agcaggggaa cgtcttcagt tgctcagtga tgcacgaggc cctgcacaat    1380 cattcaccc agaagagcct gtccctgtct ccaggcaagc ggggacgcaa aaggagaagt    1440
ggatcagggg ccacaaactt ttccctgctg aaacaggctg agatgtgga ggaaaatcca    1500 gggcccatgg tcctgcagac tcaggtgttc atcagcctgc tgctgtggat ttctggggcc    1560
tacggcagtt atgtgctgac acagcctcca agcgtctccg tggctcctgg cgaaactgca    1620
cgaatctcct gtggagggaa caatattggg actaaggtgc tgcattggta ccagcagacc    1680
ccaggacagg ctccagtgct ggtcgtgtat gacgatagtg acagacctt aggcatcccc    1740 gagcggttct ctggaagtaa ctcagggaat accgccacac tgactatttc ccgcgtcgaa    1800
```

```
gtgggcgacg aagctgatta ctattgccaa gtgtgggaca tctctaccga tcaggccgtc   1860
ttcggcggag ggactaagct gaccgtgctg ggccagccca agctgcacc ttccgtgaca   1920 ctgtttcccc ctagttcaga ggaactgcag gctaacaagg caaccctggt gtgtctgatt   1980
agcgacttct acccaggagc agtcacagtg gcatggaagc tgatagctc ccctgtcaaa   2040 gccggcgtgg aaactaccac accatctaag cagagtaaca acaagtacgc cgcttctagt   2100
tatctgagcc tgacacctga gcagtggaag tcccacagga gctattcctg ccaagtgact   2160
catgagggca gtactgtcga aaaaaccgtg gccccaacag agtgtagctg ataa         2214

<210> SEQ ID NO 12
<211> LENGTH: 2238
<212> TYPE: DNA
<213> ORGANISM: Artificial Sequence
<220> FEATURE:
<223> OTHER INFORMATION: pGX2221c

<400> SEQUENCE: 12
atggactgga cttggaggat tctgtttctg gtcgccgccg ctactgggac acacgctcag     60
gtgcagctgg tcgagagtgg ggggggagtg gtccagccag gcgatctct gaggctgagt    120 tgcgccgctt caggcttcac cttcagcact acgcaatgc actgggtgcg gcaggctcca    180
ggaaagggac tggagtgggt cgccgtgatc tcttacgacg ctaactataa gtactatgca    240
gatagtgtga aggcagatt caccattagc cgggacaact ccaagaatac actgtacctg    300
cagatgaatt ccctgcgagc agaagacacc gccgtgtact attgcgccaa agattctcag    360
ctgcgcagtc tgctgtattt cgagtggctg tctcaggggt actttgacta ttggggccag    420
ggaaccctgg tcacagtgag ctccgccagt accaagggcc catcagtgtt tcctctggct    480
ccatctagta atctacaag tggcggaact gcagccctgg gctgtctggt gaaggattac    540
ttcccagagc ccgtcacagt gtcctggaac tctggagctc tgacttccgg ggtgcatacc    600
tttcctgcag tcctgcagtc aagcgggctg tactctctgt cctctgtggt caccgtgcca    660
agttcaagcc tgggcactca gacctatatc tgcaacgtga atcacaagcc ttccaataca    720
aaagtcgaca agaaagtgga accaaagtct tgtgataaaa cacatacttg cccccccttgt    780 cctgctccag agctgctggg aggaccaagc gtgttcctgt ttccacccaa gcccaaagac    840
accctgatga ttagcaggac cccagaagtg acatgtgtgg tcgtggacgt cagccacgag    900
gaccccgaag tgaagttcaa ctggtacgtg gatggcgtcg aggtgcataa tgccaagaca    960
aaacctagga ggaacagta caacagcact atagagtcg tgtccgtcct gaccgtgctg   1020
caccaggact ggctgaacgg aaaggagtat aagtgcaaag tgtccaataa ggccctgccc   1080
gctcctatcg agaaaaccat ttctaaggct aaagggcagc cccgggaacc tcaggtgtac   1140
acactgcctc caagccgcga cgagctgacc aagaaccagg tgtccctgac atgtctggtc   1200
aaaggcttct atcccagtga tatcgccgtg gagtgggaat caaatggaca gcctgaaaac   1260
aattacaaga ccacacccc tgtgctggac agtgatggct cattctttct gtattcaaag   1320
ctgaccgtgg acaaaagccg gtggcagcag ggaaacgtct tttcatgcag cgtgatgcat   1380
gaggctctgc acaatcatta cactcagaag tccctgtctc tgagtcccgg caagcgggga   1440
cgcaaaagga gatcagggag cggcgctaca aacttctccc tgctgaagca ggcaggcgat   1500
gtggaggaaa atccaggacc catggtcctg cagacacagg tgtttatctc tctgctgctg   1560
tggattagtg gggcctatgg cgacatcgtg atgactcaga gccctgattc cctggcagtg   1620
```

```
agcctgggag agcgagcaac aattaactgt aagtcctctc agagcgtgac tttcaactac   1680
aaaaattatc tggcatggta ccagcagaag cccggacagc cacccaaact gctgatctat   1740
tgggcctcaa ctcgcgaaag cggggtgcct gaccgattct ccggatctgg gagtggcacc   1800
gattttaccc tgacaattag ttcactgcag gctgaggacg tcgcagtgta ctattgccag   1860
cagcactaca ggactcctcc aaccttcgga caggggacaa aggtcgaaat caaaactgtg   1920
gctgcacctt ccgtcttcat ttttccccct tctgacgagc agctgaagtc cggcaccgcc   1980
tctgtcgtgt gtctgctgaa caatttttac ccaagagaag ccaaggtcca gtggaaagtg   2040
gataacgctc tgcagtctgg aaatagtcag gagtcagtga cagaacagga cagcaaggat   2100
tccacttatt cactgagcaa cactctgacc ctgagcaaag cagattacga gaagcacaaa   2160
gtgtatgcct gcgaagtcac tcatcaggga ctgagctccc ccgtgaccaa gagctttaat   2220 agagggagt gttgataa                                                   2238

<210> SEQ ID NO 13
<211> LENGTH: 1437
<212> TYPE: DNA
<213> ORGANISM: Artificial Sequence
<220> FEATURE:
<223> OTHER INFORMATION: pGX9223

<400> SEQUENCE: 13
atggattgga cttggaggat tctgtttctg gtcgccgccg ctactggaac tcacgctcag     60
gtgcagctgc agcagtctgg acccggactg gtgaagcctt cacagactct gagcctgacc    120
tgcgccatct ccggcgactc tgtgagctcc aacaatgctg tctggaactg gattagacag    180
tccccatctc gggggctgga atggctggga cgaacatact ataggagcaa atggtacaat    240
gactatgctg agagtgtgaa gtcacgaatc acaattaacc cagatactag caagaatcag    300
ttctccctgc agctgaactc tgtgacaccc gaggatactg cagtctacta ttgcgcacgc    360
tccggacaca tcaccgtgtt cggagtcaat gtggacgcct ttgatatgtg gggacagggg    420
accacagtca cagtgtctag tgcaagtact aaaggcccat cagtgtttcc cctggcccct    480
tcaagcaaga gtacctcagg cggaacagcc gctctgggat gtctggtgaa ggactacttc    540
cctgagccag tcaccgtgag ctggaactcc ggagctctga ccagcggggt gcatacattt    600
cctgcagtcc tgcagtcctc tggcctgtac agcctgagtt cagtggtcac cgtgccaagc    660
tcctctctgg gaacacagac ttatatctgc aacgtgaatc acaaaccatc caatacaaag    720
gtcgacaaga aagtggaacc caaatcttgt gataagaccc atacatgccc tcccgtccca    780
gcacctgagc tgctgggcgg cccatccgtg ttcctgtttc cacccaagcc taagacaca    840 ctgatgatta gccggactcc cgaagtgacc tgcgtggtcg tggacgtgag ccacgaggac    900
cccgaagtga agttcaactg gtacgtggat ggcgtcgagg tgcataatgc caagaccaaa    960
cctagggagg aacagtacaa cagcacttat agagtcgtgt ccgtcctgac cgtgctgcac   1020
caggattggc tgaacgggaa ggagtataag tgcaaagtgt ccaacaaggc cctgccagct   1080
cccatcgaga agaccatttc taaggccaaa ggccagccac gggaaccccca ggtgtacaca   1140 ctgcctccaa gccgcgacga gctgaccaaa aaccaggtga gcctgacatg tctggtcaag   1200
ggattctatc ctagtgatat cgctgtggag tgggaatcta atgggcagcc agaaaacaat   1260
tacaagacta cccctcccgt gctggactct gatggaagtt ctttctgta ttcaaaactg   1320 accgtggaca gagccgctg gcagcagggg aacgtcttta ctgctccgt gatgcacgag   1380 gccctgcaca atcattacac tcagaaatct ctgagtctgt caccggaaa atgataa      1437
```

<210> SEQ ID NO 14
<211> LENGTH: 693
<212> TYPE: DNA
<213> ORGANISM: Artificial Sequence
<220> FEATURE:
<223> OTHER INFORMATION: pGX9231

<400> SEQUENCE: 14

```
atggtcctgc agacacaggt gtttatctct ctgctgctgt ggattagtgg cgcttacgga      60
gacatccaga tgactcagtc tcctagttca ctgtctgcaa gtgtcggcga tcgcgtgact     120
attacctgtc gaacctcaca gagcctgagc tcctacctgc attggtatca gcagaagcct     180
gggaaagcac caaagctgct gatctatgca gcctctagtc tgcagtccgg cgtgccctct     240
aggttctccg gtctggcag tggaactgac tttacactga ctatttcaag cctgcagcct     300
gaggatttcg ctacctacta ttgccagcag agcagaactt ttgggcaggg caccaaagtc     360
gaaatcaaga cagtggctgc accatccgtc ttcatttttc caccctctga cgagcagctg     420
aagagtggaa ctgcctcagt ggtgtgcctg ctgaacaatt tctaccccg ggaagccaaa     480
gtccagtgga aggtggataa cgctctgcag tcaggcaata gccaggagtc cgtgacagaa     540
caggactcta agatagtac ttattcactg agcaacaccc tgacactgag caaggcagac     600
tacgagaagc acaaagtgta tgcctgcgaa gtgaccccacc aggggctgag cagtccagtg     660
accaaatctt tcaacagggg agaatgttga taa                                  693
```

<210> SEQ ID NO 15
<211> LENGTH: 1437
<212> TYPE: DNA
<213> ORGANISM: Artificial Sequence
<220> FEATURE:
<223> OTHER INFORMATION: pGX9310

<400> SEQUENCE: 15

```
atggattgga catggaggat tctgtttctg gtcgccgccg caactggaac tcacgctcag      60
gtgcagctgc agcagtcagg gcctggcctg gtgaagccca gccagaccct gtccctgaca     120
tgcgccatct ccggcgactc tgtgagctcc aacaatgccg tgtggaactg gatcaggcag     180
tccccttctc gcggcctgga gtggctggga aggacctact atagaagcaa gtggtacaat     240
gactatgccg agagcgtgaa gtccaggatc accatcaacc cagatacatc taagaatcag     300
ttcagcctgc agctgaactc cgtgaccccc gaggatacag ccgtgtacta ttgcgccaga     360
tccggccaca tcaccgtgtt cggcgtgaat gtggacgcct ttgatatgtg gggcagggc     420
accacagtga ccgtgtctag cgcctctaca aagggcccaa gcgtgtttcc actggcaccc     480
tcctctaaga gcacctccgg cggcacagcc gccctgggct gtctggtgaa ggactacttc     540
ccagagcccg tgaccgtgtc ttggaacagc ggcgccctga ccagcggagt gcacacattt     600
cctgccgtgc tgcagagctc cggcctgtac tccctgtcta gcgtggtgac cgtgccatcc     660
tctagcctgg gcacccagac atatatctgc aacgtgaatc acaagccaag caatacaaag     720
gtggacaaga aggtggagcc caagtcctgt gataagaccc acacatgccc tccctgtcct     780
gcaccagagc tgctgggcgg cccaagcgtg ttcctgtttc cacccaagcc taaggacacc     840
ctgatgatct ctcggacccc cgaggtgaca tgcgtggtgg tggacgtgag ccacgaggac     900
cccgaggtga agttcaactg gtacgtggat ggcgtggagg tgcacaatgc caagacaaag     960
cctagggagg agcagtacaa ctccacctat agagtggtgt ctgtgctgac agtgctgcac    1020
```

```
caggattggc tgaacggcaa ggagtataag tgcaaggtgt ccaataaggc cctgcccgcc    1080
cctatcgaga agaccatctc taaggcaaag ggacagcctc gggagccaca ggtgtacaca    1140
ctgcctccat cccgcgacga gctgaccaag aaccaggtgt ctctgacatg tctggtgaag    1200
ggcttctatc cttctgatat cgccgtggag tgggagagca atggccagcc agagaacaat    1260
tacaagacca cacccctgt gctggactcc gatggctctt tctttctgta tagcaagctg     1320
accgtggaca agtcccgctg gcagcaggc aacgtgtttt cttgtagcgt gatgcacgaa     1380
gcactgcaca accattacac ccagaagtca ctgtcactgt ccccaggaaa atgataa       1437

<210> SEQ ID NO 16
<211> LENGTH: 693
<212> TYPE: DNA
<213> ORGANISM: Artificial Sequence
<220> FEATURE:
<223> OTHER INFORMATION: pGX9311

<400> SEQUENCE: 16
atggtgctgc agacccaggt gtttatttcc ctgctgctgt ggattagcgg cgcatacggc      60
gacattcaga tgactcagag ccccttcaagc ctgtccgcct ctgtgggcga cagggtgacc    120
atcacatgca gaaccagcca gtccctgagc tcctacctgc actggtatca gcagaagcca    180
ggcaaggccc ccaagctgct gatctacgca gcctctagcc tgcagagcgg cgtgccttcc    240
cggttctctg gcagcggctc cggcaccgac tttaccctga caatctcctc tctgcagcca    300
gaggatttcg ccacatacta ttgccagcag tcccgcacct tggccaggg cacaaaggtg     360 gagatcaaga ccgtggccgc cccctccgtg ttcatctttc ccccttctga cgagcagctg    420
aagtctggca cagccagcgt ggtgtgcctg ctgaacaatt tctaccctag ggaggccaag    480
gtgcagtgga aggtggataa cgccctgcag tccggcaatt ctcaggagag cgtgaccgag    540
caggactcca aggattctac atattctctg agcaacaccc tgacactgag caaggccgat    600
tacgagaagc acaaggtgta tgcctgtgag gtcactcacc aggggctgtc atcacccgtc    660
accaaatcct ttaataggg agaatgttga taa                                  693
```

DNA MONOCLONAL ANTIBODIES TARGETING INFLUENZA VIRUS

CROSS-REFERENCE TO RELATED APPLICATIONS

This application is the U.S. national stage application filed under 35 U.S.C. § 371 claiming benefit to International Patent Application No. PCT/US17/31213, filed May 5, 2017, which claims priority to U.S. Provisional Application No. 62/332,381, filed May 5, 2016 and U.S. Provisional Application No. 62/376,162, filed Aug. 17, 2016, each of which is incorporated by reference herein in its entirety.

TECHNICAL FIELD

The present invention relates to a composition comprising a recombinant nucleic acid sequence for generating one or more synthetic antibodies, including anti-Influenza Hemagglutinin antibodies, and functional fragments thereof, in vivo, and a method of preventing and/or treating disease in a subject by administering said composition.

BACKGROUND

Despite promising innovations, influenza vaccines and antiviral drugs do not provide full protection from seasonal infection, and provide little immediate defense against novel and potentially pandemic viral strains. Broadly cross-protective monoclonal antibodies have been developed with the aim of providing protection against highly divergent influenza viruses.

Thus, there is a need in the art for improved compositions and methods for the treatment of influenza.

SUMMARY

The present invention is directed to a nucleic acid molecule encoding one or more synthetic antibodies, wherein the nucleic acid molecule comprises at least one selected from the group consisting of a) a nucleotide sequence encoding an anti-influenza hemagglutinin (HA) synthetic antibody; and b) a nucleotide sequence encoding a fragment of an anti-HA synthetic antibody.

In one embodiment, the anti-HA synthetic antibody is selected from the group consisting of an antibody that binds to the globular head of influenza HA and an antibody that binds to the fusion subdomain of influenza HA.

In one embodiment, the nucleic acid molecule comprises at least one nucleotide sequence selected from the group consisting of a first nucleotide sequence encoding a first anti-HA antibody; and a second nucleotide sequence encoding a second anti-HA antibody.

In one embodiment, the nucleic acid molecule comprises a nucleotide sequence encoding a cleavage domain.

In one embodiment, the nucleic acid molecule comprises a nucleotide sequence encoding a variable heavy chain region and a variable light chain region of anti-HA.

In one embodiment, the nucleic acid molecule comprises a nucleotide sequence encoding a constant heavy chain region and a constant light chain region of human IgG1κ.

In one embodiment, the nucleic acid molecule comprises a nucleotide sequence encoding a polypeptide comprising a variable heavy chain region of anti-HA; a constant heavy chain region of human IgG1κ; a cleavage domain; a variable light chain region of anti-HA; and a constant light chain region of IgG1κ.

In one embodiment, the nucleic acid molecule comprises a nucleotide sequence which encodes a leader sequence.

In one embodiment, the nucleic acid molecule comprises an expression vector.

In one embodiment, the invention provides a composition comprising the nucleic acid molecule. In one embodiment, the composition further comprises a pharmaceutically acceptable excipient.

In one embodiment, the present invention provides a method of preventing or treating an influenza infection in a subject, comprising administering to the subject the nucleic acid or a composition described herein. In one embodiment, the influenza infection is an influenza A infection. In one embodiment, the influenza infection is an influenza B infection.

In one embodiment, the present invention provides novel sequences for producing monoclonal antibodies in mammalian cells or in viral vectors.

BRIEF DESCRIPTION OF THE DRAWINGS

FIG. 1 shows the influenza hemagglutinin variable regions where anti-influenza antibody 5J8 binds.

FIGS. 3A and 3B, depicts results from experiments demonstrating DMAb plasmid DNA constructs are expressed in 293T cells. FIG. 3A depicts ELISA results where supernatant and lysate Human IgG1κ expression was determined by quantitative ELISA (N=3 transfection replicates, Mean±SEM.) FIG. 3B depicts a representative western blot demonstrating supernatant and lysate heavy- and light-chain peptide cleavage.

FIGS. 4A and 4B, depicts results from experiments demonstrating DMAb are expressed in mouse serum following intramuscular DNA electroporation. Mice were injected with 5J8 or FI6 plasmid DNA followed by intramuscular electroporation. Human IgG1κ antibody levels in mouse sera were determined by quantitative ELISA. FIG. 4A depicts results demonstrating anti-influenza DMAb were expressed from 53 ng/mL to 1.1 µg/mL over baseline Day-0 pre-bleed levels seven days after delivery in BALB/c mice. Optimization strategies of site delivery and formulation enhanced DMAb expression >3-fold. FIG. 4B depicts results of DNA dose escalation in nude mice. Following delivery of 300 µg plasmid DNA to immune-compromised nude mice, peak FI6 expression reached 2.6 µg/mL. Expression of DMAb endured over ten weeks. (N=5, Mean±SEM.)

FIG. 14, comprising FIG. 14A depicts human IgG expression in cell supernatants (left) and lysates (right) was quantified by ELISA. 293T cells were transfected with FluA or FluB DMAb plasmid constructs, or empty plasmid (pVax1). (n=3, ±SEM). FIG. 14B depicts western blot of human IgG heavy-chain and light-chain peptides in reduced DMAb-transfected 293T cell supernatants (S) and lysates (L) (left), and purified protein monoclonal antibody FluA and FluB (IgG, right). FIG. 14C depicts DMAb human IgG in CAnN.Cg-Foxn1$^{nu}$/Crl nude mouse sera after intramuscular electroporation (IM-EP) (Day 0) with 100-300 μg of FluA plasmid DNA. (n=5, ±SEM). FIG. 14D depicts DMAb human IgG in CAnN.Cg-Foxn1$^{nu}$/Crl nude mouse sera after intramuscular electroporation (IM-EP) (Day 0) with 100-300 μg of FluB plasmid DNA. (n=5, ±SEM). FIG. 14E depicts levels of DMAb human IgG in BALB/c mouse sera 5 days post-administration of 100-300 μg of FluA DMAb plasmid DNA. Dotted line indicates limit of detection (LOD). (n=5, ±SEM). FIG. 14F depicts levels of DMAb human IgG in BALB/c mouse sera 5 days post-administration of 100-300 μg of FluB DMAb plasmid DNA. Dotted line indicates limit of detection (LOD). (n=5, ±SEM).

FIG. 15, comprising FIG. 15A depicts) ELISA binding $EC_{50}$ values (reciprocal dilution) for individual mouse serum samples to influenza A HA proteins from Group 1 (H1 A/California/07/2009 H1N1, H2 A/Missouri/2006 H2N3, H5 A/Vietnam/1203/2004 H5N1, H6 A/teal/Hong Kong/W312/97 H6N1, H9 A/chicken/Hong Kong/G9/1997 H9N2) and Group 2 (H3 A/Perth/16/2009 H3N2, H7 A/Netherlands/219/2003 H7N7). FIG. 15B depicts ELISA Binding $EC_{50}$ values (reciprocal dilution) for individual mouse serum samples to influenza B HA proteins from the Yamagata (Yam B/Florida/4/2006) and Victoria (Vic B/Brisbane/60/2008) lineages. FIG. 15C depicts Neutralization $IC_{50}$ values (reciprocal dilution) for individual mouse serum samples against Yam B/Florida/4/2006 and Vic B/Malaysia/2506/2004 viruses. (n=5, ±SD).

FIG. 16, comprising FIG. 16A depicts human IgG in mouse sera at the time of influenza infection. FIG. 16B depicts Kaplan-Meier survival curves of BALB/c mice challenged with influenza A. (n=10). FIG. 16C depicts weight of BALB/c mice following influenza A challenge. Dotted line indicates 25% maximum weight loss. (n=10, ±SEM). FIG. 16D depicts human IgG in mouse sera at the time of influenza infection. FIG. 16E depicts Kaplan-Meier survival curves of BALB/c mice challenged with influenza A. (n=10). FIG. 16F depicts weight of BALB/c mice following influenza A challenge. Dotted line indicates 25% maximum weight loss. (n=10, ±SEM).

FIG. 17, comprising FIG. 17A depicts human IgG in mouse sera at the time of infection. Dotted line indicates LOD. (n=10, ±SD). FIG. 17B depicts Kaplan-Meier survival curves of BALB/c mice challenged with influenza B. (n=10). FIG. 17C depicts weight of BALB/C mice following influenza B challenge. Dotted line indicates 25% maximum weight loss. (n=10, ±SEM). FIG. 17D depicts human IgG in mouse sera at the time of infection. Dotted line indicates LOD. (n=10, ±SD). FIG. 17E depicts Kaplan-Meier survival curves of BALB/c mice challenged with influenza B. (n=10). FIG. 17F depicts weight of BALB/c mice following influenza B challenge. Dotted line indicates 25% maximum weight loss. (n=10, ±SEM).

FIG. 18, comprising FIG. 18A depicts total human IgG levels in mice sera at the time of infection. (n=8±SD). FIG. 18B depicts Influenza A-specific and B-specific human IgG in mouse serum at the time of infection quantified by HA binding ELISA. (n=8, ±SD). FIG. 18C depicts Kaplan-Meier survival curves following initial infection with A/California/07/2009. FIG. 18D depicts Kaplan-Meier survival curves following initial infection with B/Florida/4/2006. FIG. 18E depicts experiments where twenty-eight days following initial infection, surviving mice received homologous influenza re-infection. Kaplan-Meier survival curves following re-infection, compared to mice receiving neither DMAb/IgG treatment nor initial infection (naïve). FIG. 18F depicts experiments where twenty-eight days following initial infection, surviving mice received homologous influenza re-infection. Kaplan-Meier survival curves following re-infection, compared to mice receiving neither DMAb/IgG treatment nor initial infection (naïve).

Figure depicts the results of experiments demonstrating the enhancement of in vivo DMAb expression. Serum DMAb human IgG expression in mice five days following sequentially revised administrations of 200 μg FluB plasmid DNA. Plasmid DNA was delivered to BALB/c mice via intramuscular electroporation alone (IM-EP), or via IM-EP with hyaluronidase formulation (Hya+IM-EP). Furthermore, plasmid transgene insert sequences were DNA codon-optimized and RNA optimized for enhanced expression (Opt+Hya+IM-EP). All other studies were performed Opt+Hya+IM-EP. (n=5 animals per group, mean±SEM).

Figure 20:
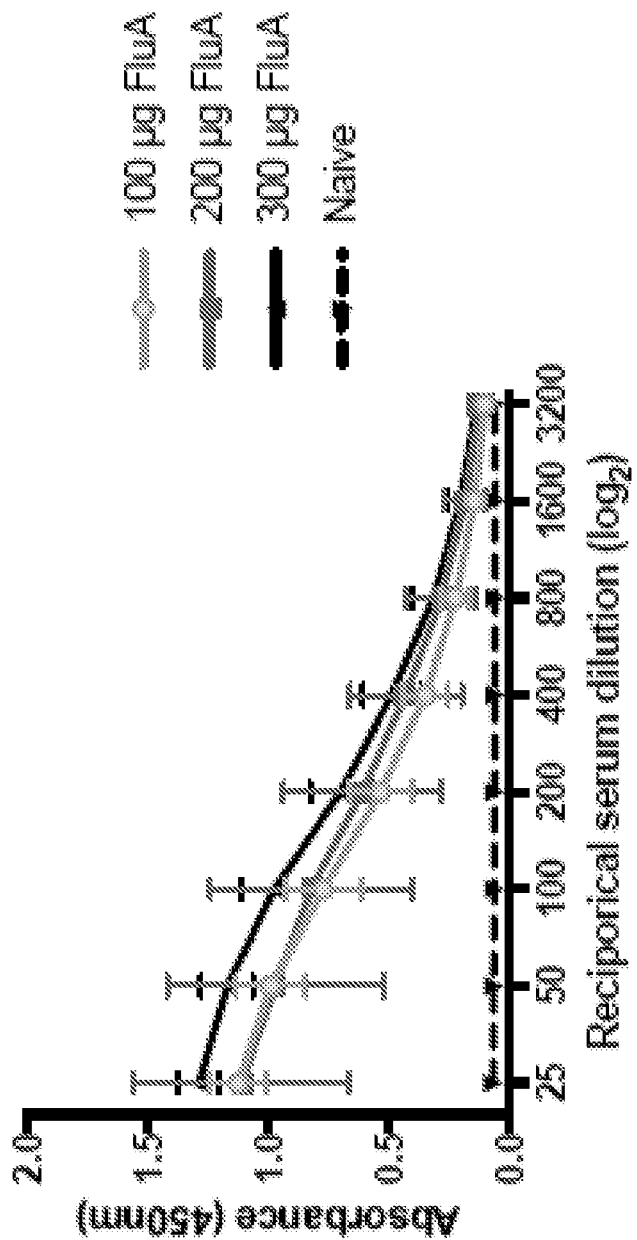

FIG. 20 depicts the results of experiments demonstrating FluA DMAb in mouse sera binds influenza A hemagglutinin H10. Sera from BALB/c mice collected 5 days after treatment with 100-300 μg of FluA DMAb plasmid DNA were serially diluted and added to 96-well plates coated with influenza A Group 2 recombinant H10 antigen (A/Jiangxi-Donghu/346/2013 H10N8) (IBT Bioservices). DMAb binding was detected with HRP-conjugated secondary antibody donkey anti-human IgG (1:5,000) and developed using SigmaFast OPD substrate (Sigma-Aldrich). Absorbance was measured at 450 nm. Sera from un-treated (naïve) mice served as a control. (n=5 animals per group, mean±SD).

Figures 21A, 21B:
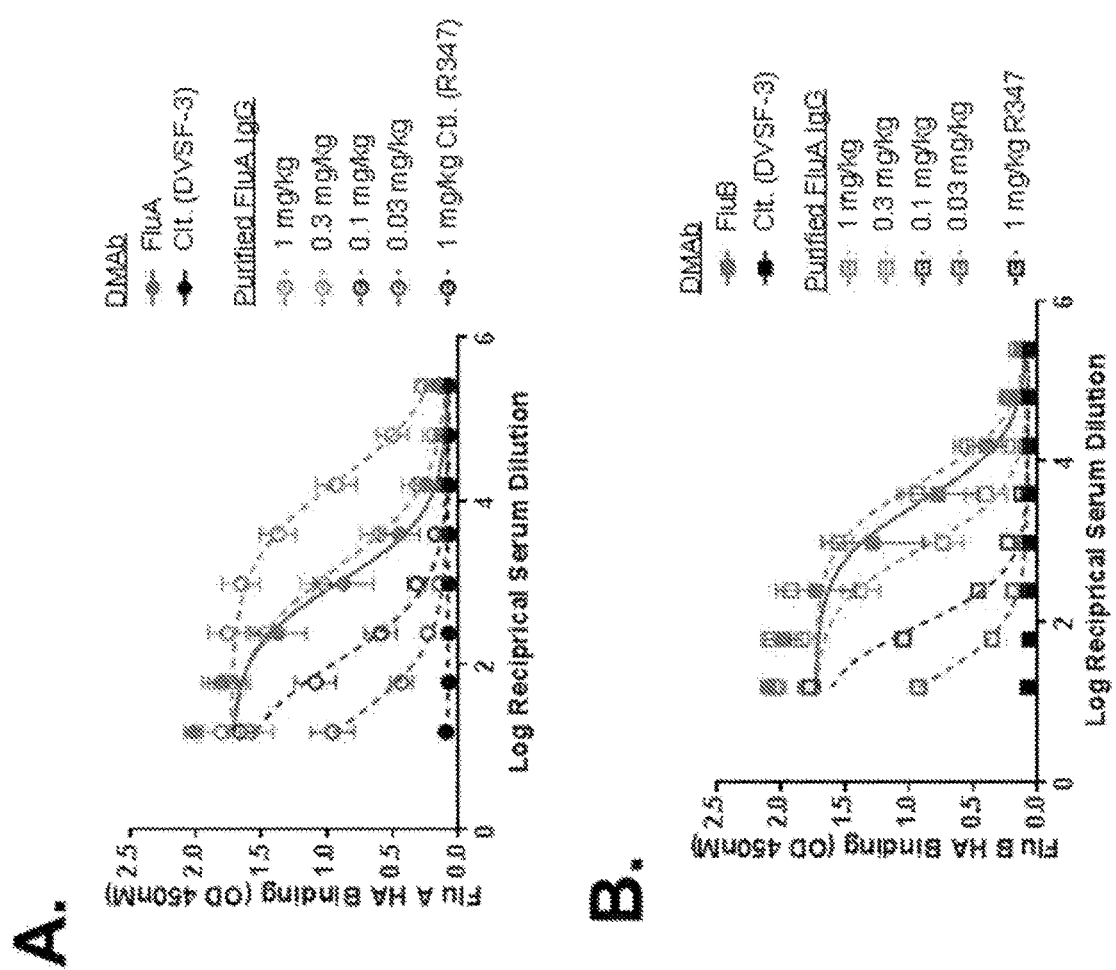
Figures 22A, 22B:
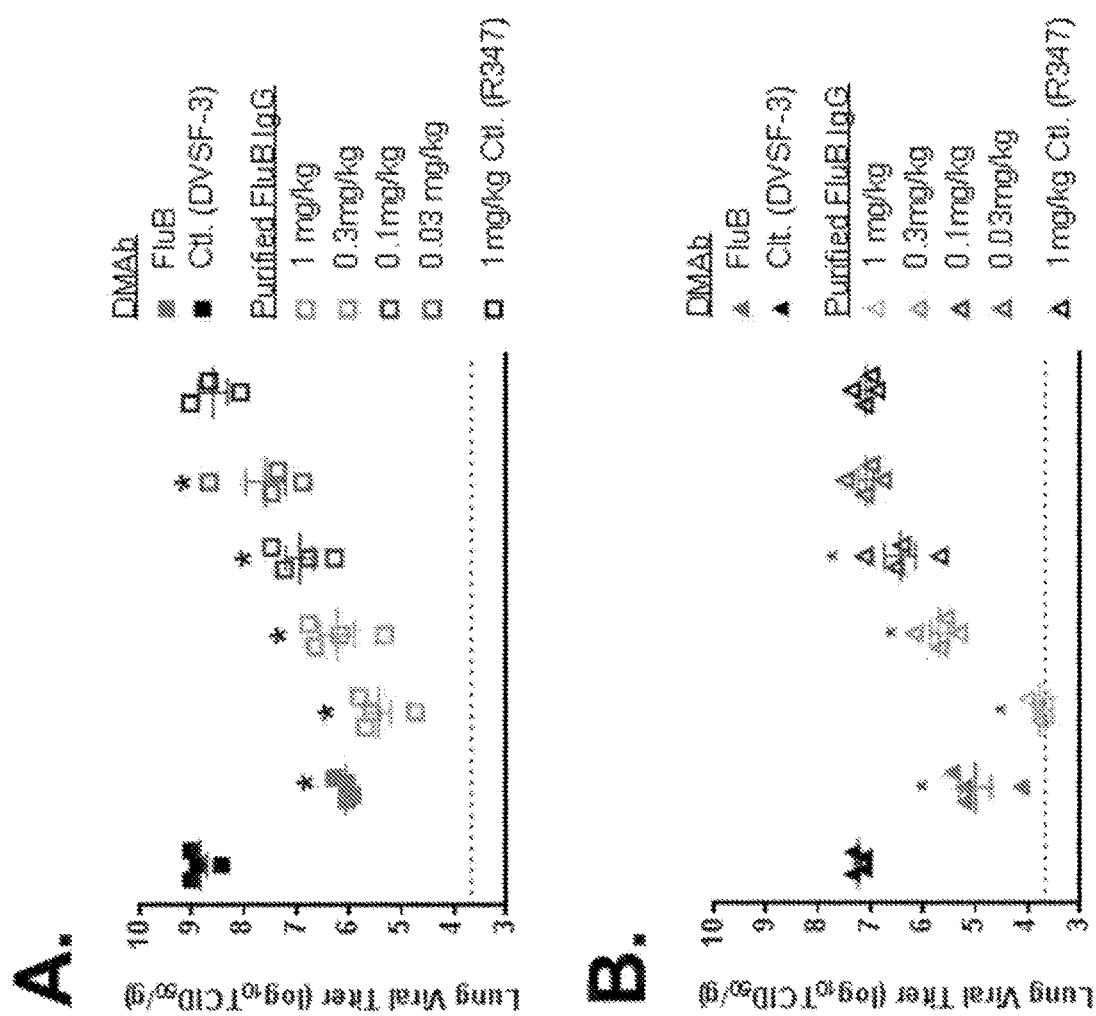

FIG. 21, comprising FIG. 21A and FIG. 21B, depicts results of experiments demonstrating FluA and FluB DMAb expressed in vivo produce functional IgG at similar levels as purifed IgG. FIG. 21A depicts reactivity to purified H1 HA protein from A/California/7/2009 H1 of serum samples from animals treated with FluA plasmid DNA, purified anti-influenza IgG protein, or irrelevant control DMAb (DVSF-3). Serum was harvested on the day of influenza infection and tested for HA reactivity by binding ELISA. FIG. 20B depicts reactivity to purified Victoria lineage HA protein from B/Brisbane60/2008 Victoria of serum samples from animals treated with FluB plasmid DNA, purified anti-influenza IgG protein, or irrelevant control DMAb (DVSF-3). Serum was harvested on the day of influenza infection and tested for HA reactivity by binding ELISA FIG. 22, comprising FIG. 22A and FIG. 22B, depicts results of experiments demonstrating FluB significantly lowers influenza B viral burden in lungs. BALB/c mice were treated with 200 μg FluB DMAb plasmid DNA or irrelevant DMAb control (DVSF-3) 5 days prior to infection. Separate groups received 0.03-1 mg/kg FluB purified IgG protein or irrelevant control IgG R347 i.p. one day prior to infection. FIG. 22A depicts Lung Viral Titers on day 5 post-infection with B/Malaysia/2508/2004. FIG. 22B depicts Lung Viral Titers on day 5 post-infection with B/Florida/4/2006. (n=4, ±SEM). Dotted line indicates LOD. * Significant reduction in viral titers compared to control DMAb DVSF-3 group by Student's t test.

Figures 23A, 23B, 23C, 23D:
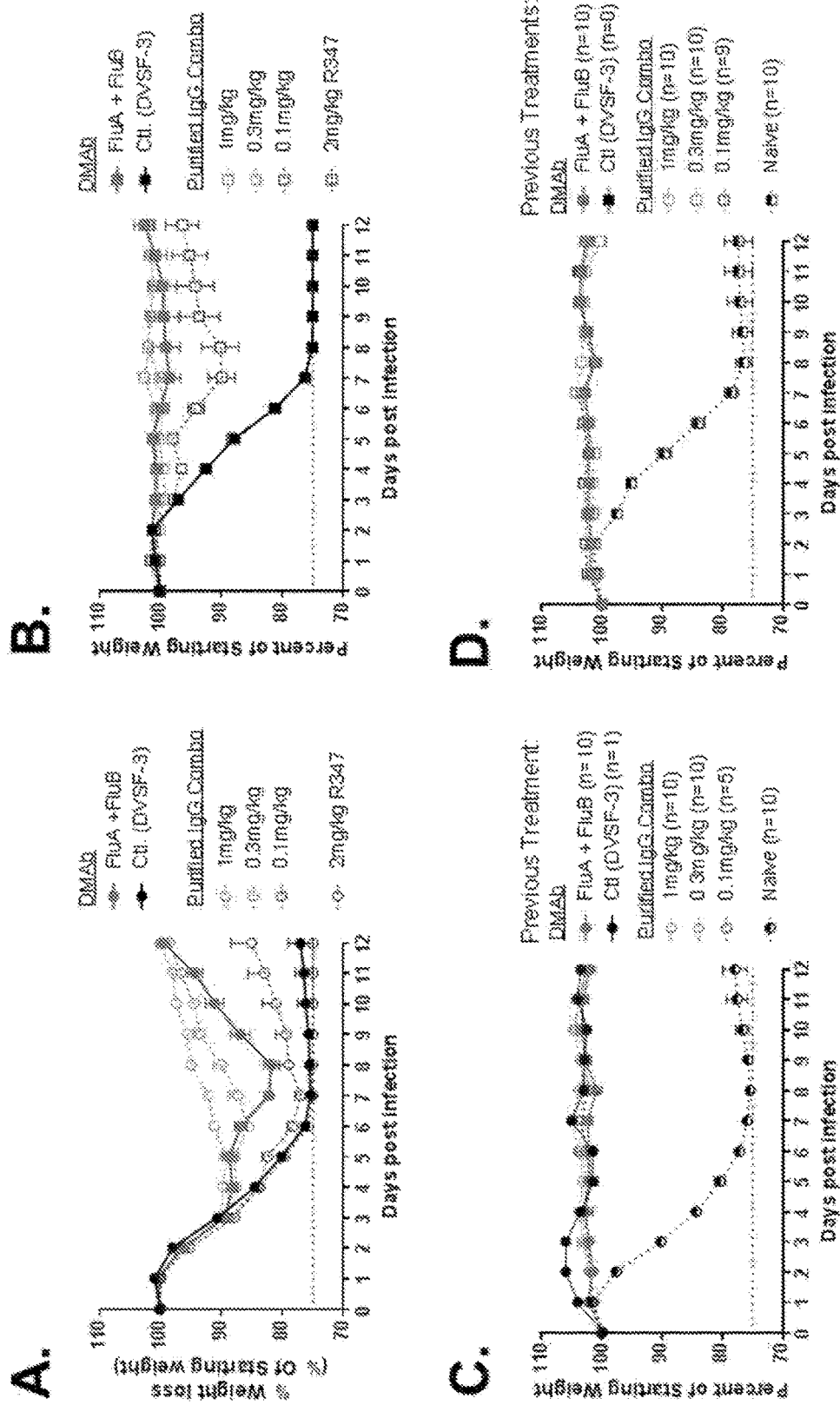

FIG. 23, comprising FIG. 23A through FIG. 23D, depicts results of experiments demonstrating co-administration of FluA and FluB DMAb protects mice from lethal influenza challenge and homologous re-challenge. BALB/c mice received both FluA and FluB DMAb. Separate groups were treated with 0.1-1 mg/kg of a combination of FluA and FluB protein IgG one day prior to infection. FIG. 23A depicts body weight loss of animals infected with A/California/7/2009 (n=10, ±SEM). FIG. 23B depicts body weight loss of animals infected with B/Florida/4/2006 (n=10, ±SEM). FIG. 23C depicts body weight loss following homologous influenza re-challenge of surviving mice with A/California/7/2009 28 days following initial infection. FIG. 23D depicts body weight loss following homologous influenza re-challenge of surviving mice with B/Florida/4/2006 28 days following initial infection.

Figures 24A, 24B, 24C, 24D:
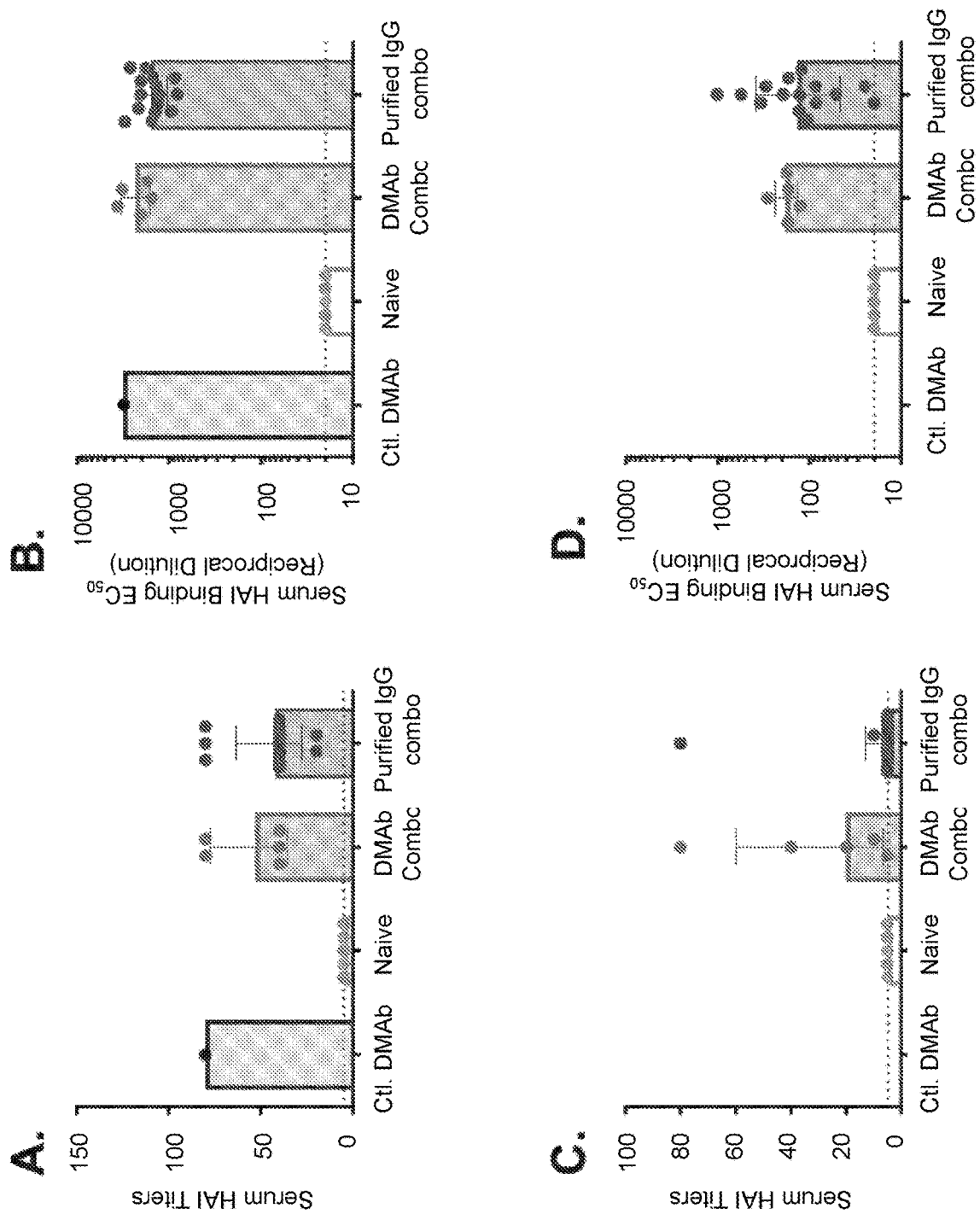

FIG. 24, comprising FIG. 24A through FIG. 24D, depicts results of experiments demonstrating the serum reactivity of DMAb-treated mice 21 days post-infection. Functional assays performed with sera from surviving BALB/c mice collected 21 days after infection with A/California/7/2009 or B/Florida/4/2006. FIG. 24A depicts hemagglutination inhibition activity (reciprocal dilution) against infecting virus A/California/07/2009. FIG. 24B depicts ELISA binding EC50 values (reciprocal dilution) to influenza A/California/07/2009 HA protein. FIG. 24C depicts hemagglutination inhibition activity (reciprocal dilution) against infecting virus B/Florida/4/2006. FIG. 24D depicts ELISA binding EC50 values (reciprocal dilution) to influenza B HA protein.

DETAILED DESCRIPTION

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody directed against influenza antigen.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen immunization induced immune response. The synthetic antibodies are able to effectively bind and neutralize a range of antigens. The synthetic antibodies are highly specific for the target. The synthetic antibodies are also able to effectively protect against disease and/or promote survival from disease.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment. In some instances, the antigen is an influenza antigen.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. The term nucleic acid also encompasses nucleic acid analogs and non-native nucleic acids. For example, the nucleic acids may be modified, e.g. may comprise one or more modified nucleobases or modified sugar moieties. The backbone of the nucleic acid may comprise one or more peptide bonds as in peptide nucleic acid (PNA). The nucleic acid may comprise a base analog such as non-purine or non-pyrimidine analog or nucleotide analog. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Composition

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an influenza antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding anti-HA antibody. In one embodiment, the nucleotide sequence encoding anti-HA antibody comprises codon optimized nucleic acid sequences encoding the variable VH and VL regions of anti-HA. In one embodiment, the nucleotide sequence encoding anti-HA antibody comprises codon optimized nucleic acid sequences encoding CH and CL regions of human IgG1κ.

In one embodiment, the nucleic acid molecule comprises a nucleotide sequence encoding a FluA heavy chain anti-HA. In one embodiment, the nucleic acid molecule comprises a nucleotide sequence encoding a FluA light chain anti-HA. In one embodiment, the nucleic acid molecule comprises a nucleotide sequence encoding a FluA heavy chain anti-HA and a nucleotide sequence encoding a FluA light chain anti-HA. In one embodiment, the nucleic acid molecule comprises a nucleotide sequence encoding a FluB heavy chain anti-HA and a nucleotide sequence encoding a FluB light chain anti-HA.

In one embodiment, the anti-HA antibody binds the globular head of influenza HA. In one embodiment, the anti-HA antibody is FJ8. In one embodiment, the anti-HA antibody binds the fusion subdomain of influenza HA. In one embodiment, the anti-HA antibody is FI6. In one embodiment, the anti-HA antibody is cross reactive to FluA H5 and H7 HA proteins. In one embodiment, the anti-HA antibody is reactive to FluB HA proteins.

In one embodiment, the nucleic acid molecule comprises a nucleotide sequence encoding anti-HA antibody comprising an amino acid sequence selected from SEQ ID NOs:1-8, or a variant thereof or a fragment thereof. In one embodiment, the nucleic acid encoding anti-HA antibody comprises a nucleotide sequence of any of SEQ ID NOs:9-12, or a variant thereof or a fragment thereof. In one embodiment, the nucleic acid encoding anti-HA antibody comprises a RNA molecule transcribed from a DNA sequence of any of SEQ ID NOs:9-12, or a variant thereof or a fragment thereof.

In one embodiment, the nucleic acid molecule comprises a nucleotide sequence encoding anti-HA antibody comprising an amino acid sequence having at least about 80%, at least about 85%, at least about 90% or at least about 95% identity over the entire length of an amino acid sequence selected from SEQ ID NOs:1-8. In one embodiment, the nucleic acid molecule comprises a nucleotide sequence encoding a fragment of an anti-HA antibody comprising an amino acid sequence having at least about 80%, at least about 85%, at least about 90% or at least about 95% identity over the entire length of an amino acid sequence selected from SEQ ID NOs:1-8.

In one embodiment, the nucleic acid molecule comprises a nucleotide sequence at least about 80%, at least about 85%, at least about 90% or at least about 95% identity over the entire length of the nucleotide sequence to a nucleotide sequence selected from SEQ ID NOs:9-16. In one embodiment, the nucleic acid molecule comprises a fragment of a nucleotide sequence having at least about 80%, at least about 85%, at least about 90% or at least about 95% identity over the entire length of the nucleotide sequence to a nucleotide sequence selected from SEQ ID NOs:9-16.

In one embodiment, the nucleic acid molecule comprises RNA sequence transcribed from a DNA sequence at least about 80%, at least about 85%, at least about 90% or at least about 95% identity over the entire length of the DNA selected from SEQ ID NOs:9-16. In one embodiment, the nucleic acid molecule comprises a fragment of an RNA sequence transcribed from a DNA sequence at least about 80%, at least about 85%, at least about 90% or at least about 95% identity over the entire length of the DNA selected from SEQ ID NOs:9-16.

In one embodiment, the nucleotide sequence encoding anti-HA antibody comprises codon optimized nucleic acid sequences encoding the variable VH and VL regions of anti-HA. In one embodiment, the VH region of HA comprises an amino acid sequence of SEQ ID NOs:5, 7, 9 or 10, or a variant thereof or a fragment thereof. In one embodiment, the VH region of HA comprises an amino acid at least 85%, at least 90% or at least 95% or more homologous to SEQ ID NOs:5, 7, 9 or 10, or a fragment thereof. In one embodiment, the VL region of HA comprises an amino acid sequence of one of SEQ ID NOs: 6-10, or a variant thereof or a fragment thereof. In one embodiment the nucleotide sequence variable VH region of HA comprises a nucleotide sequence of SEQ ID NOs:13 or 15, or a variant thereof or a fragment thereof. In one embodiment the nucleotide sequence variable VH region of HA comprises a nucleotide sequence at least 85%, at least 90% or at least 95% or more homologous to SEQ ID NOs:13 or 15, or a variant thereof or a fragment thereof. In one embodiment the nucleotide sequence variable VL region of HA comprises a nucleotide sequence of SEQ ID NOs:14, 15 or 16, or a variant thereof or a fragment thereof. In one embodiment the nucleotide sequence variable VL region of HA comprises a nucleotide sequence at least 85%, at least 90% or at least 95% or more homologous to SEQ ID NOs:14, 15 or 16, a fragment thereof In one embodiment the nucleotide sequence variable VL region of HA comprises a RNA molecule transcribed from a DNA sequence of any of SEQ ID NOs: 14, 15 or 16, or a variant thereof or a fragment thereof.

In one embodiment, the composition comprises at least two nucleic acid molecules. In one embodiment, the nucleic acid molecules are selected from a nucleic acid encoding FluA Heavy Chain anti-HA, a nucleic acid encoding FluA Light Chain anti-HA, a nucleic acid encoding FluA anti-HA, and a nucleic acid encoding FluB anti-HA. In one embodiment, the nucleic acid molecules are selected from a nucleic acid encoding one of SEQ ID NO:1-8. In one embodiment, the nucleic acid molecules are selected from a nucleic acid encoding a peptide at least 90% homologous to SEQ ID NO:1-8. In one embodiment, the composition comprises a nucleic acid comprising a nucleotide sequence encoding SEQ ID NO:1 and a comprises a nucleic acid comprising a nucleotide sequence encoding SEQ ID NO:2. In one embodiment, the composition comprises a nucleic acid comprising a nucleotide sequence comprising SEQ ID NO:9 and a nucleic acid comprising a nucleotide sequence comprising SEQ ID NO:10.

The composition of the invention can treat, prevent and/or protect against any influenza infection. In certain embodiments, the composition can treat, prevent, and or/protect against influenza A infection. In certain embodiments, the composition can treat, prevent, and or/protect against an influenza A virus from group H1 or group H3. In another embodiment, the influenza A virus is a pmH1 influenza virus. In other embodiments, the composition can treat, prevent, and or/protect against influenza B infection.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. In one embodiment, the synthetic antibody can provide increased survival of the disease in the subject over the expected survival of a subject having the disease who has not been administered the synthetic antibody. In various embodiments, the synthetic antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the synthetic antibody can provide increased protection against the disease in the subject over the expected protection of a subject who has not been administered the synthetic antibody. In various embodiments, the synthetic antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include at least one heterologous nucleic acid sequence or one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include the heterologous nucleic acid sequence encoding the protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and W094/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by one of SEQ ID NOs: 9-16. In another embodiment, the nucleotide sequence comprises an RNA sequence transcribed by a DNA sequence encoding the polypeptide sequence of SEQ ID NOs: 9-16, or a variant thereof or a fragment thereof. Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. Antibody

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab)$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker, including a cancer marker.

b. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

e. Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcyR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcyR1a, and thus, the modified antibody does not enhance or cause ADE of disease associated with the antigen, but still neutralizes the antigen.

5. Antigen

The synthetic antibody is directed to the antigen or fragment or variant thereof. The antigen can be a nucleic acid sequence, an amino acid sequence, or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof.

In some embodiments, the antigen is a self-antigen. In one embodiment, the antigen is influenza HA. In one embodiment, the antigen is the globular head of influenza HA. In one embodiment, the antigen is the fusion subdomain of influenza HA a. Foreign Antigens In some embodiments, the antigen is foreign. A foreign antigen is any non-self substance (i.e., originates external to the subject) that, when introduced into the body, is capable of stimulating an immune response.

(1) Viral Antigens

The foreign antigen can be a viral antigen, or fragment thereof, or variant thereof.

The viral antigen may comprise an antigen from influenza virus. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be derived from multiple strains of influenza A serotype H1, serotype H2, a hybrid sequence derived from different sets of multiple strains of influenza A serotype H1, or derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be derived from hemagglutinin antigen sequences from a plurality of influenza A virus strains of one serotype such as a plurality of influenza A virus strains of serotype H1 or of serotype H2. The antigen may be a hybrid hemagglutinin antigen sequence derived from combining two different hemagglutinin antigen sequences or portions thereof. Each of two different hemagglutinin antigen sequences may be derived from a different set of a plurality of influenza A virus strains of one serotype such as a plurality of influenza A virus strains of serotype H1. The antigen may be a hemagglutinin antigen sequence derived from hemagglutinin antigen sequences from a plurality of influenza B virus strains.

In some embodiments, the influenza antigen can be H1 HA, H2 HA, H3 HA, H5 HA, or a BHA antigen.

b. Self Antigens

In some embodiments, the antigen is a self antigen. A self antigen may be a constituent of the subject's own body that is capable of stimulating an immune response. In some embodiments, a self antigen does not provoke an immune response unless the subject is in a disease state, e.g., an autoimmune disease.

Self antigens may include, but are not limited to, cytokines, antibodies against viruses such as those listed above including HIV and Dengue, antigens affecting cancer progression or development, and cell surface receptors or transmembrane proteins.

6. Excipients and Other Components of the Composition

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to about 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. Method of Generating the Synthetic Antibody

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. Method of Identifying or Screening for the Antibody

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. Method of Delivery of the Composition

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application, Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S.

Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. Method of Treatment

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

In certain embodiments, the invention provides a method of treating protecting against, and/or preventing an influenza infection, or diseases or disorders associated with an influenza infection. For example, in one embodiment, the method treats, protects against, and/or prevents influenza A. In one embodiment, the method treats, protects against, and/or prevents a respiratory infection. Exemplary diseases or disorders treated or prevented by way of the administration of the composition of the invention, includes, but is not limited to viral or bacterial pneumonia, dehydration, and ear infections and sinus infections.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The composition dose can be between 1 µg to 10 mg active component/kg body weight/time, and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

The present invention has multiple aspects, illustrated by the following non-limiting examples.

11. Examples

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The studies presented herein demonstrate the generation of functional anti-IL-6 and anti-CD126 "DNA monoclonal antibodies" (DMAb) via intramuscular electroporation of plasmid DNA. Codon-optimized variable region DNA sequences from anti-IL-6 and anti-CD126 monoclonal antibodies were synthesized onto a human IgG1 constant domain. Plasmid DNA encoding antibody was delivered to BALB/c mice (FIG. 1). This study supports DMAb as an alternative to existing biologic therapies, and provides a novel method to further define the role of in vivo IL-6 signaling in immune pathologies.

The methods and materials are now described
Antibody DNA Sequences & Cloning:
Anti-influenza 5J8 and FI6 antibody clonal sequences were previously published (Krause et al., 2011, J virol 85(20):10905-8; Corti et al., 2011, Science 333(6044):850-6). Variable region DNA sequences were codon-optimized and synthesized into a constant human IgG1κ backbone. Constructs were cloned into a modified pVax-1 mammalian expression plasmid. A furin/2A peptide cleavage site was included for separation of heavy and light-chain peptides. (FIG. 1).
Transfections:
Approx. $1\times10^6$ 293T cells were transfected with 0.5 µg plasmid DNA using GeneJammer (Agilent Technologies). Cell supernatants and lysates were collected 48 hours later.
DMAb Electroporation:
100-300 µg of plasmid DNA was delivered i.m. to the quadriceps followed by electroporation with a CELLECTRA® 3P device (Inovio Pharmaceuticals, Plymouth Meeting, PA) as previously described (Flingai et al., 2015, Sci Rep 29(5):12616; Muthumani et al., 2013, Hum Vaccin Immunother 9(10):2253-62).
ELISA & Western Blots:
Human IgG1κ were bound to anti-human-$F_e$ fragments and detected with anti-kappa-light-chain HRP conjugated antibody (Bethyl), with quantification against a human IgG1κ standard antibody. Binding to recombinant HA (Immune-Technologies) was detected with HRP-conjugated anti-human-IgG secondary antibody (Sigma-Aldrich). Western blots were developed with conjugated anti-human IgG 800 nm antibody (Licor).

Figure 2:
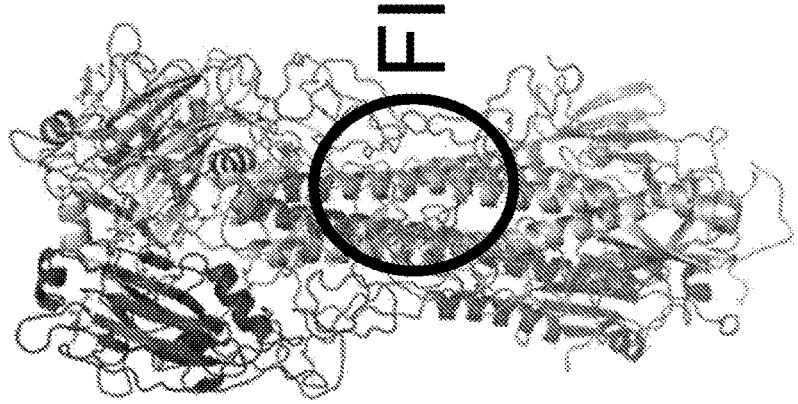
FIG. 2 shows the influenza hemagglutinin variable regions where anti-influenza antibody FI6 binds.
Figure 3:
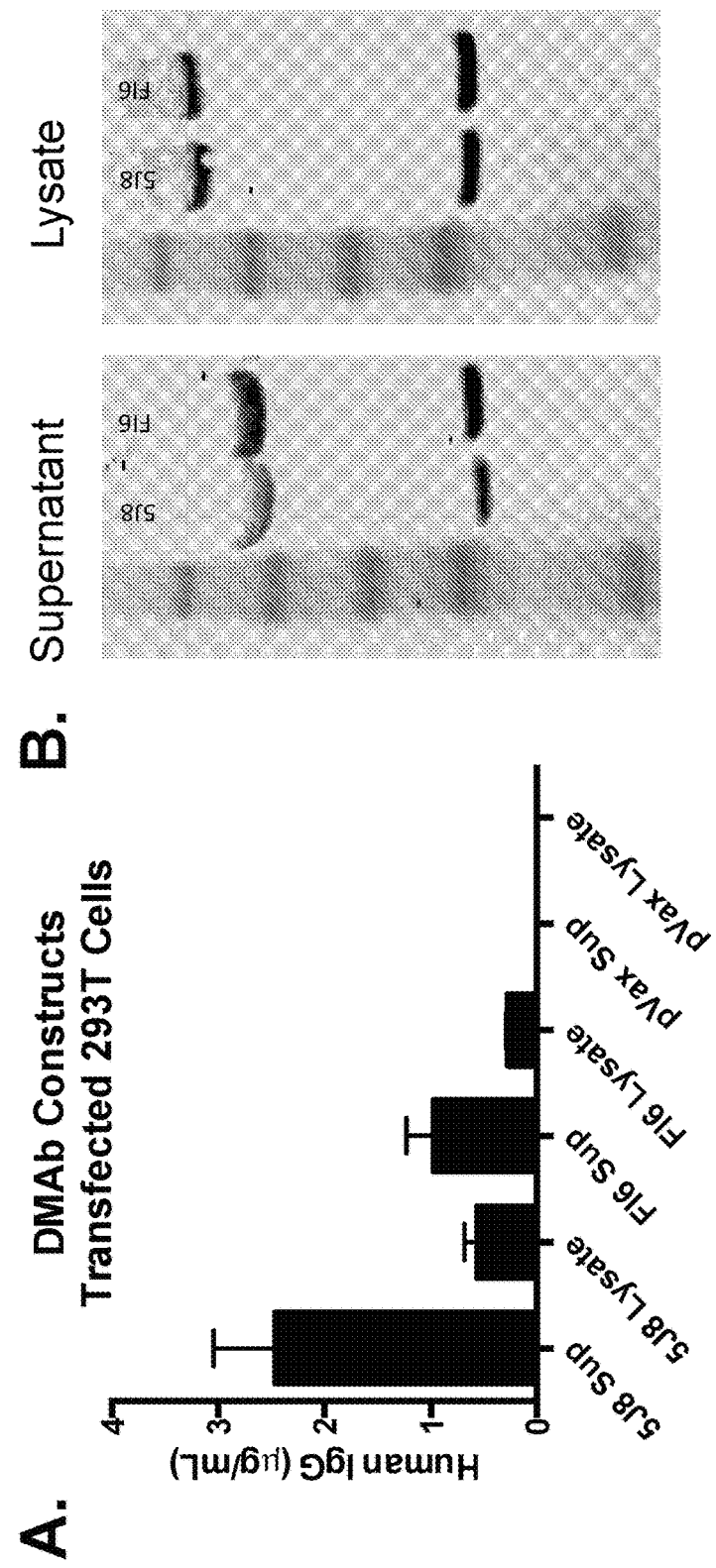
FIG. 3, comprising
Figure 4:
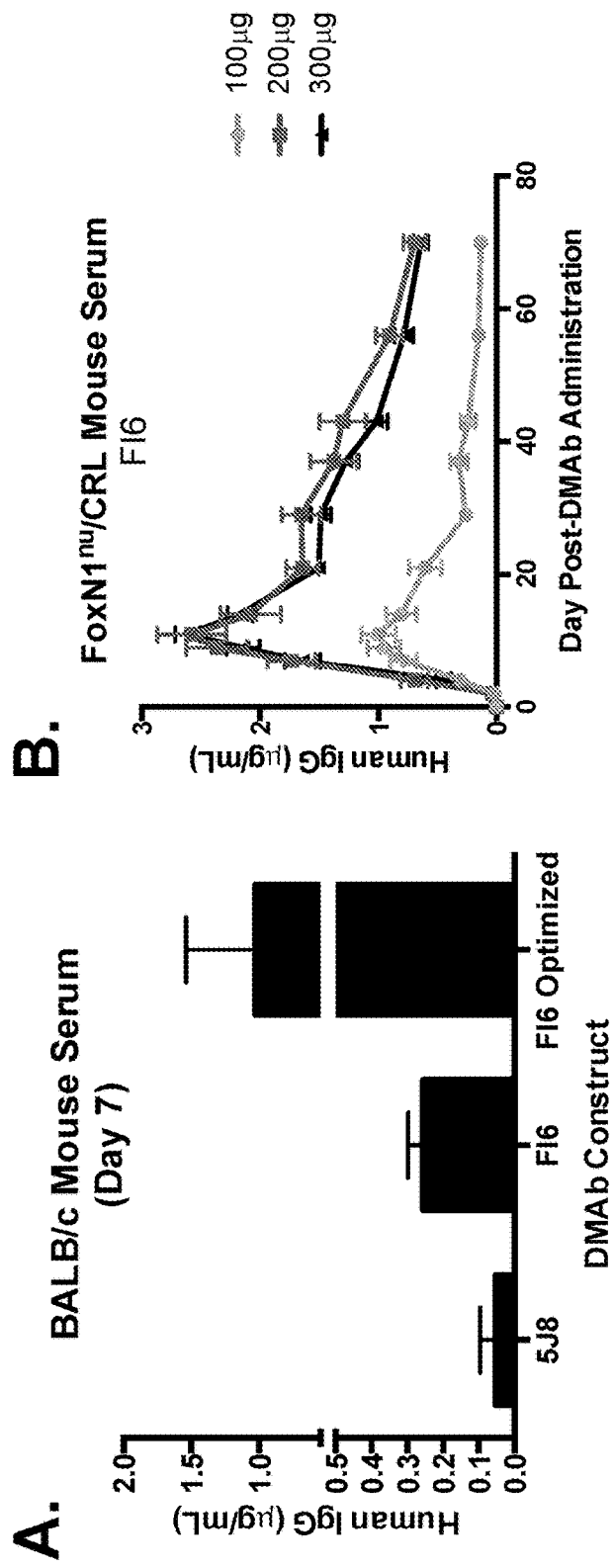
FIG. 4, comprising

The results of the experiments are now described
Intramuscular Electroporation of Plasmid DNA Encoding Anti-Influenza Antibody Generates Monoclonal Antibodies In Vivo
Monoclonal antibody variable VH and VL amino acid sequences were DNA codon optimized. The codon optimized DNA was synthesized with human IgG1κ antibody constant CH and CL region DNA sequences. The engineered DNA sequence was cloned into a modified pVax-1 expression vector. The plasmid construct was injected intramuscularly followed by electroporation with CELLECTRA® device (Inovio Pharmaceuticals). Expression and function of human IgG1 DMAb produced in vivo was measured.
DMAb Constructs Contain Variable Regions from Published Anti-Influenza Monoclonal Antibodies
The DMAb constructs contain variable regions from anti-influenza monoclonal antibodies, 5J8 (anti-HA 5J8) and FI6 (anti-HA FI6). FJ8 Binds to a receptor binding pocket on variable globular head and is cross-reactive to multiple influenza-A H1 viruses. FI6 binds to a relatively conserved fusion sub-domain and gives broad neutralization of Group 1 & Group 2 influenza-A viruses (FIG. 2).
DMAb Constructs are Expressed and Secreted from Transfected 293T Cells
Experiments were conducted to evaluate the expression and secretion of anti-influenza-HA antibodies 5J8 and FI6 encoded by the DMAb constructs. HEK 293T cells were transfected with plasmid DNA carrying 5J8 or FI6 constructs. Empty plasmid served as a negative control. Human IgG1κ expression was determined by quantitative ELISA and Western blots were performed to detect supernatant and lysate heavy and light-chain peptide cleavage and expression (FIG. 3A-FIG. 3B). As shown in FIG. 3B, anti-HA 5J8 and anti-HA FI6 is observed in HEK 293T supernatant and HEK 293T lysate demonstrating the ability for the DMAb construct to induce the expression and secretion of anti-HA 5J8 and anti-HA FI6.

Robust Serum Levels of DNA Monoclonal Antibodies Achieved Following Intramuscular DNA Electroporation Experiments were conducted to evaluate whether the DMAb induced the expression of anti-HA 5J8 and anti-HA FI6 in vivo. BALB/c mice were injected with 5J8 or FI6 plasmid DNA followed by intramuscular electroporation. Seven days later, serum human IgG1κ antibody levels were determined by ELISA. As shown in FIG. 3A and FIG. 3B, high levels of anti-HA 5J8 and anti-HA FI6 antibody are produced in mouse serum following DNA electroporation of muscle.

Figure 5:
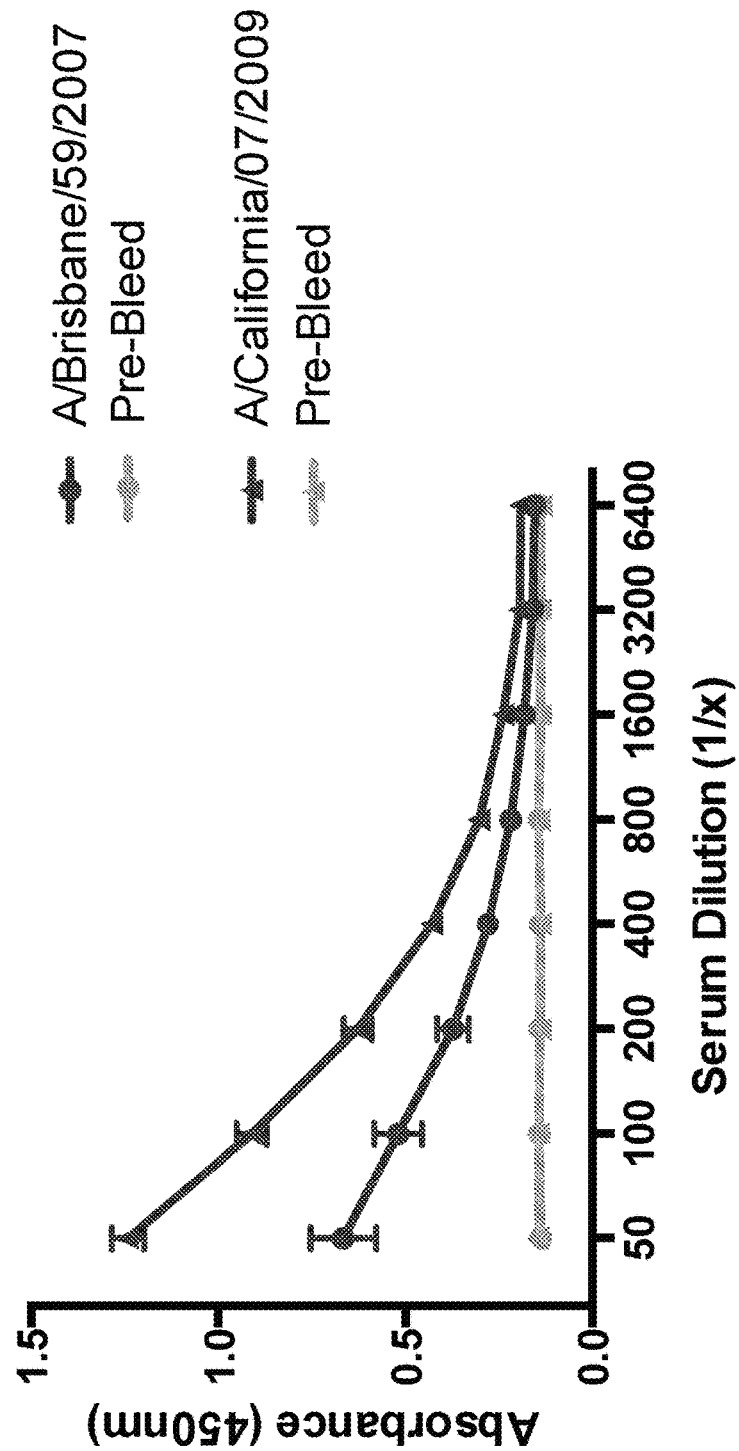
FIG. 5 depicts results from experiments demonstrating DMAb from mouse sera retain ability to bind hemagglutinin antigen. Nude mice received FI6 (300 µg) plasmid DNA with intramuscular electroporation. Four weeks later, serum DMAb binding to recombinant influenza-A H1 hemagglutinin antigen was determined by ELISA. (N=5, Mean±SEM.)
Figure 6:
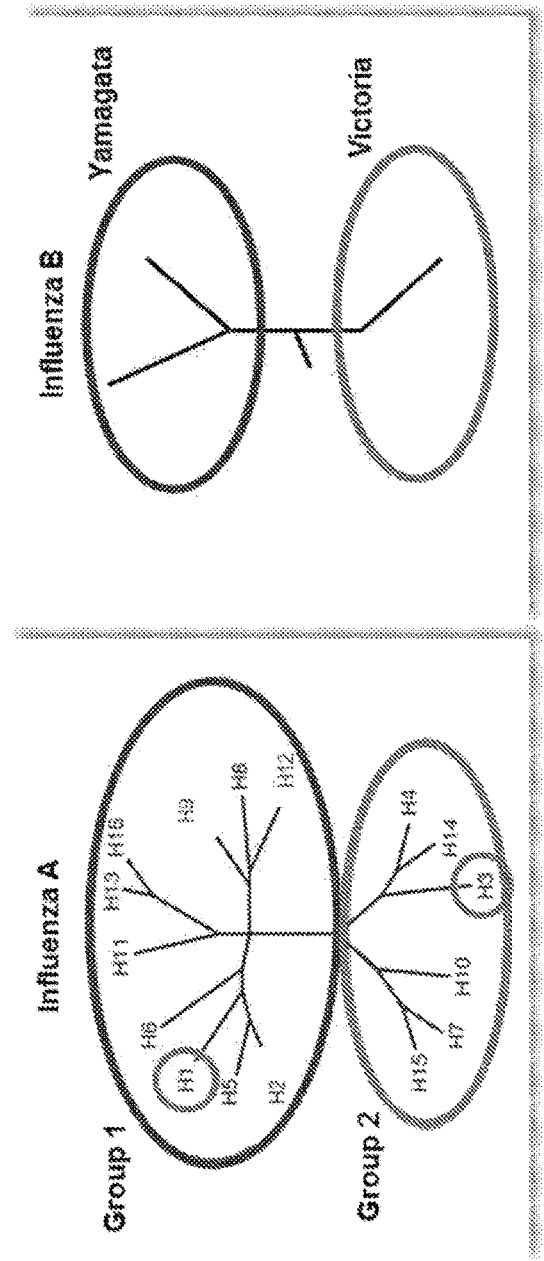
FIG. 6 depicts phylogenetic trees of Influenza A strains and Influenza B strains demonstrating the diversity of clinically relevant influenza viruses.
Figure 7:
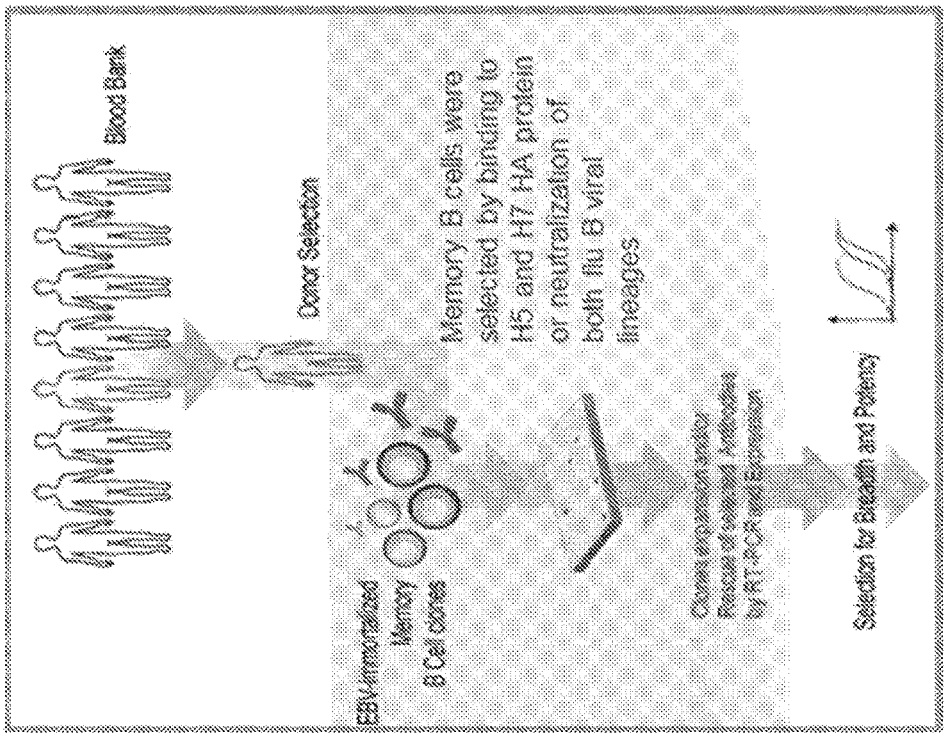
FIG. 7 depicts results of experiments demonstrating isolated human monoclonal antibodies (mAbs) directed toward influenza A and B have broad cross-reactivity. Influenza A-specific FluA mAb broadly neutralizes seasonal and pandemic viruses across both group 1 and 2. FluB mAb potently neutralizes viruses from both lineages of influenza B.
Figure 7:
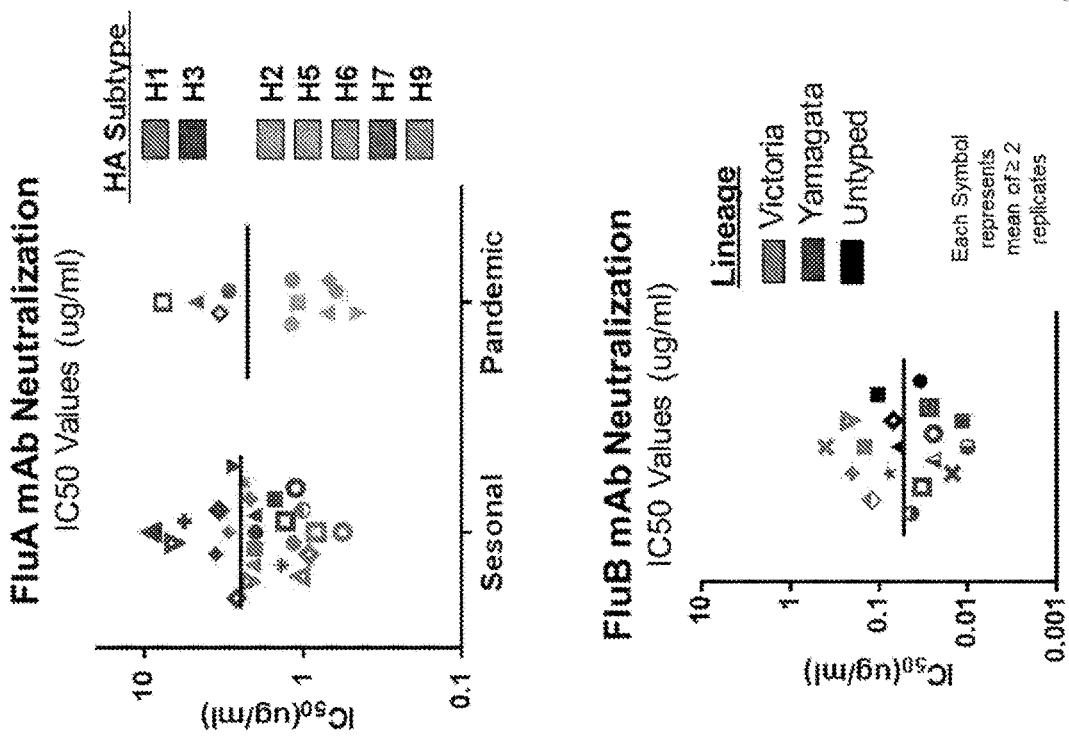
Figure 8:
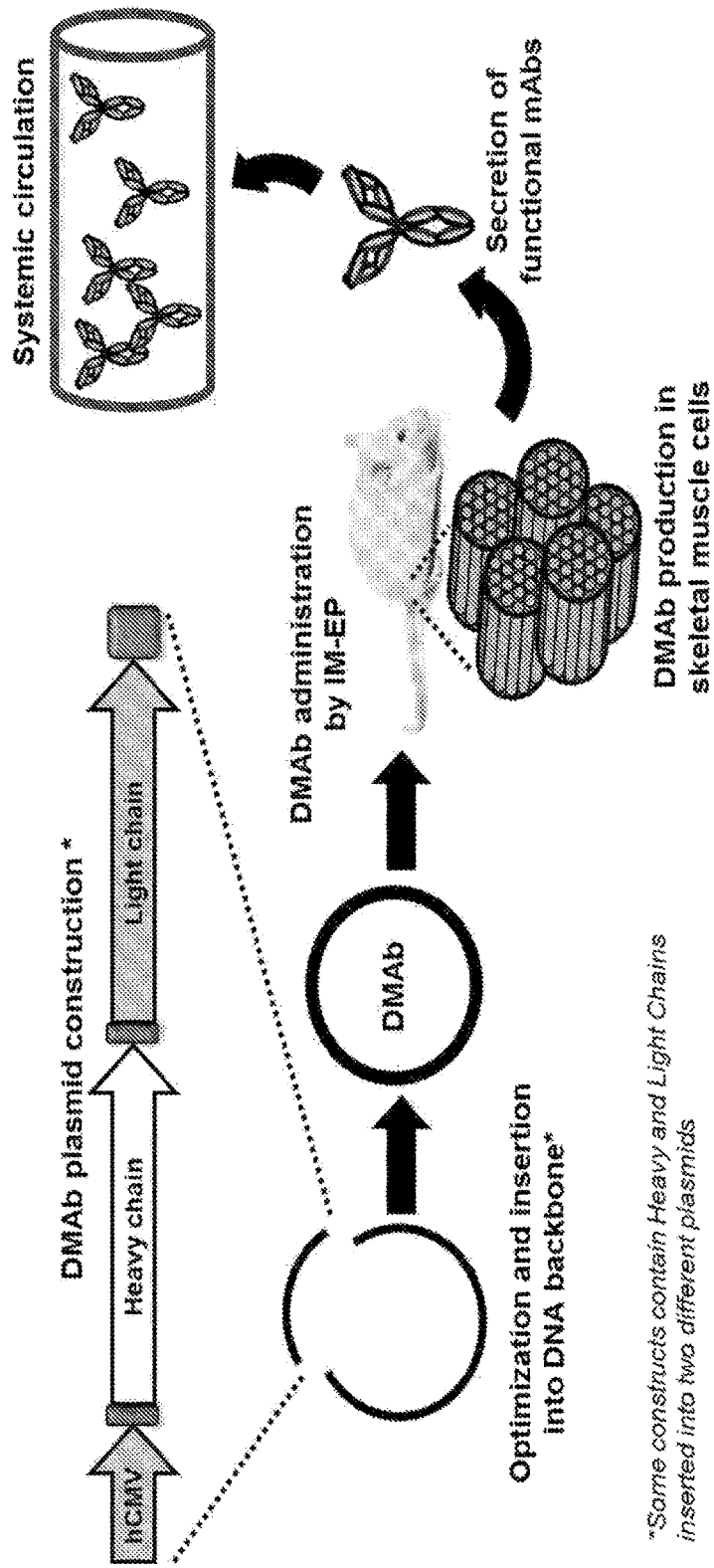
FIG. 8 depicts a schematic of DMAb plasmid construction and production of functional mAbs.
Figure 9:
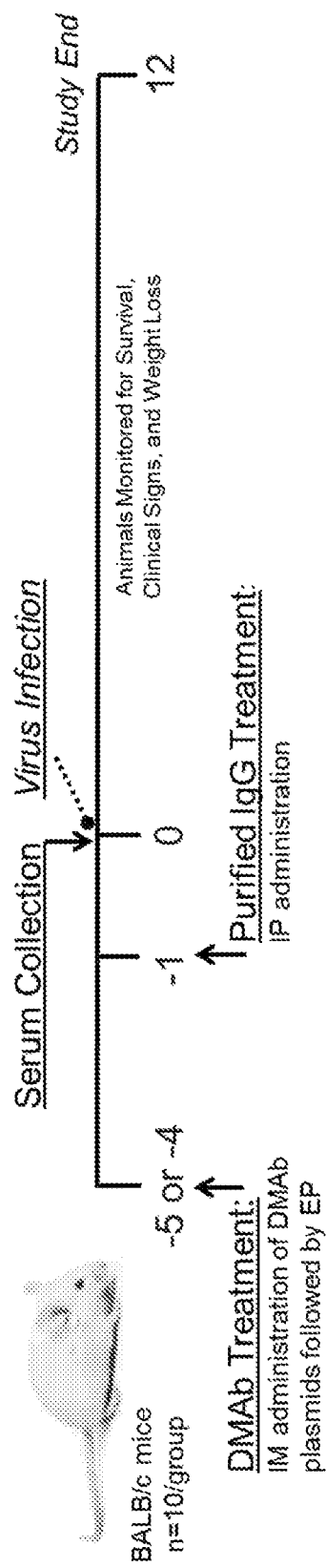
FIG. 9 depicts a schematic of the influenza lethal challenge study design.
Figure 10:
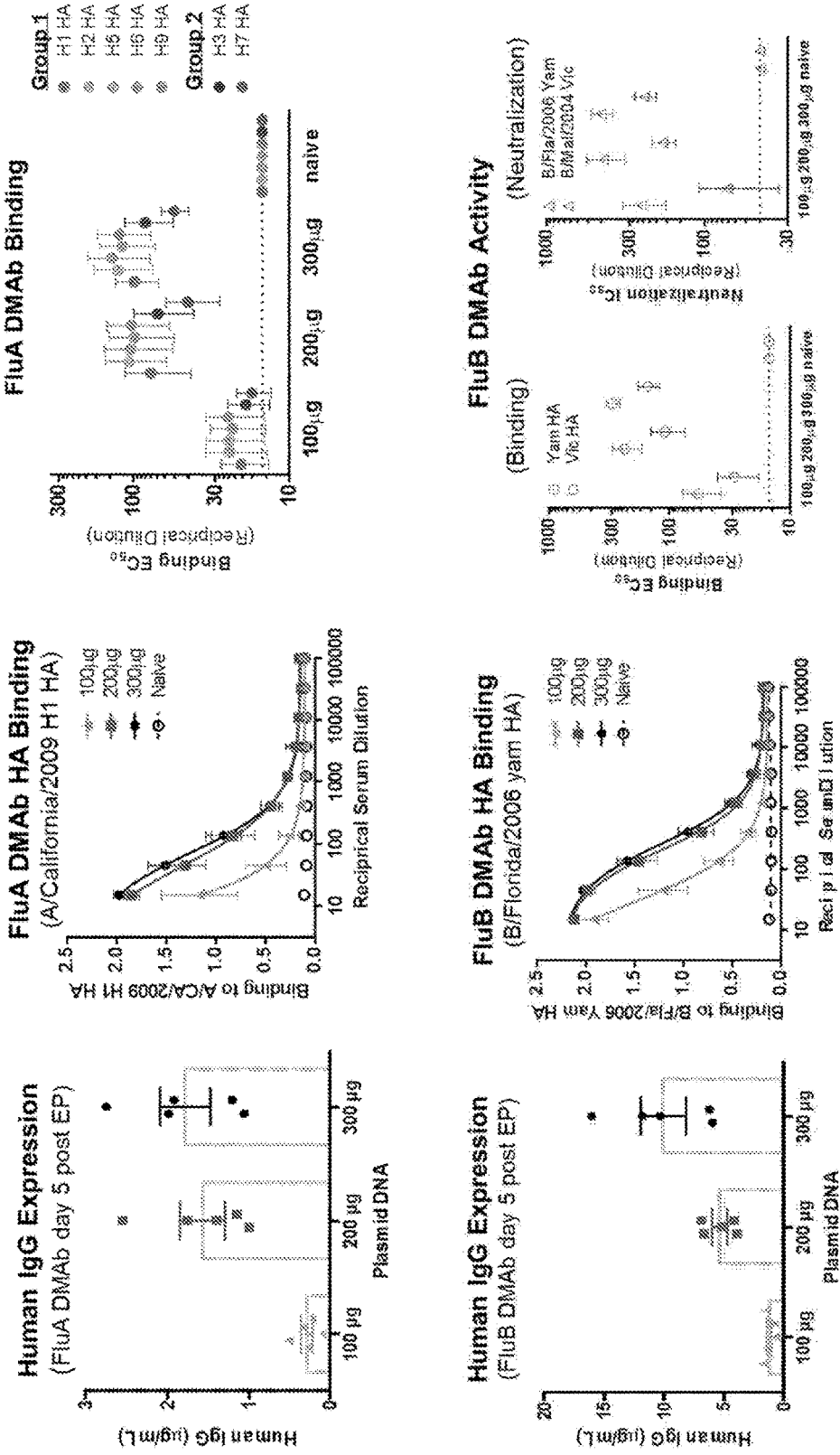
FIG. 10 depicts results of experiments demonstrating FluA and FluB DMAb serum expression and functionality. Serum was collected day 5 post EP of FluA DMAb (top row) and FluB DMAb (bottom row) and evaluated for human IgG expression, binding activity to a variety of HA proteins and neutralization activity.
Figure 11:
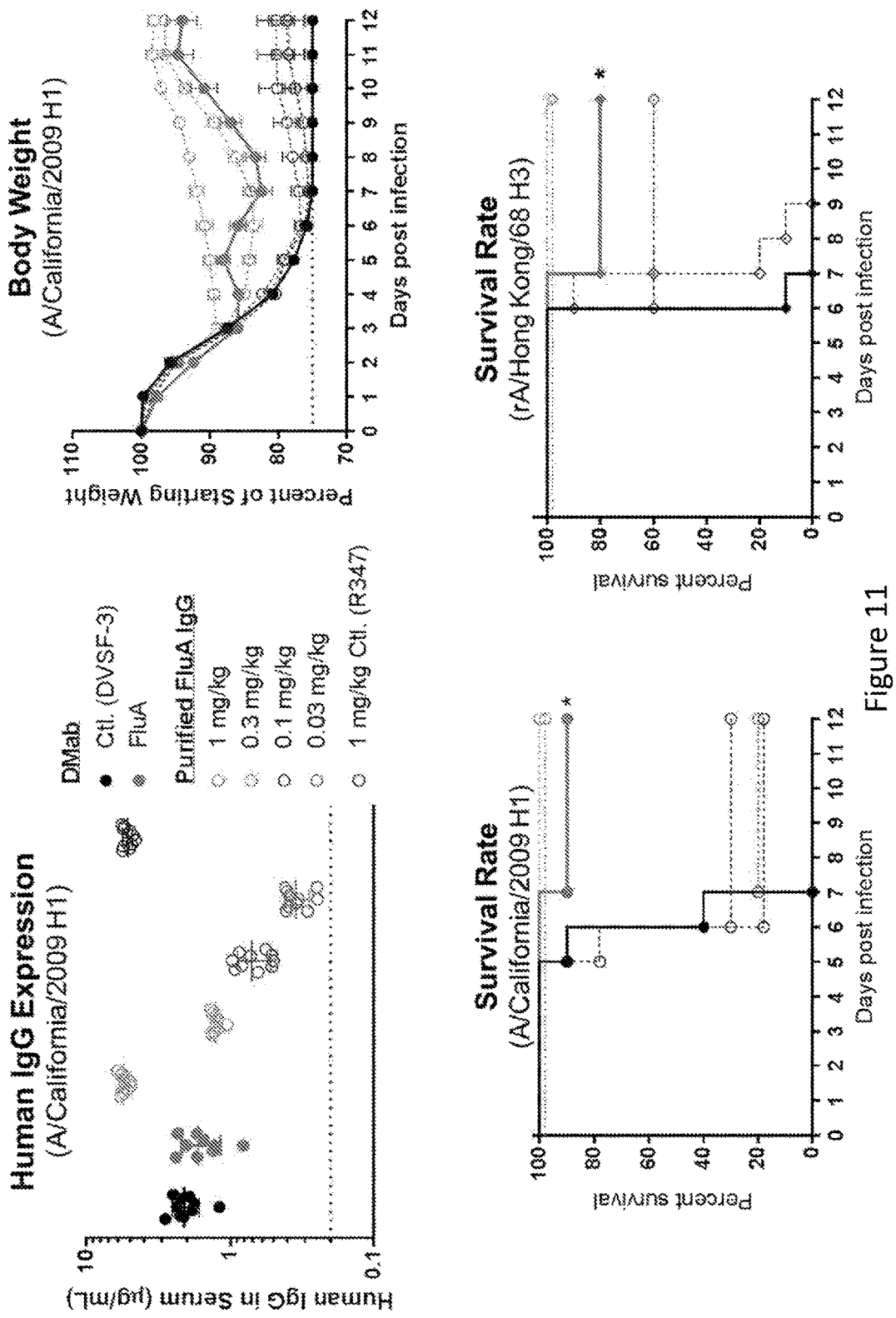
FIG. 11 depicts results of experiments demonstrating FluA DMAb protects mice from lethal influenza A infection to similar levels as purified FluA IgG at 0.3 mg/kg. Serum concentrations of DMAb in relation to purified IgG at time of infection. Body weight loss, and survival rate after challenge with lethal influenza A infection, * significant survival benefit of FluA DMAb compared to control DMAb $p<0.0001$ by log-rant test.

DNA Monoclonal Antibodies Generated Following Intramuscular DNA Electroporation Retain their Ability to Bind Diverse Target HA Antigens Experiments were conducted to investigate the functionality of expressed anti-HA FI6. BALB/c mice were injected with 300 μg plasmid DNA followed by intramuscular electroporation. Four weeks later, DMAb binding to recombinant influenza-A H1 HA antigen was determined by ELISA. As shown in FIG. 5, the expressed antibodies bind to target A/Brisbane/59/2007 and A/California/07/2009 targets.

Figure 12:
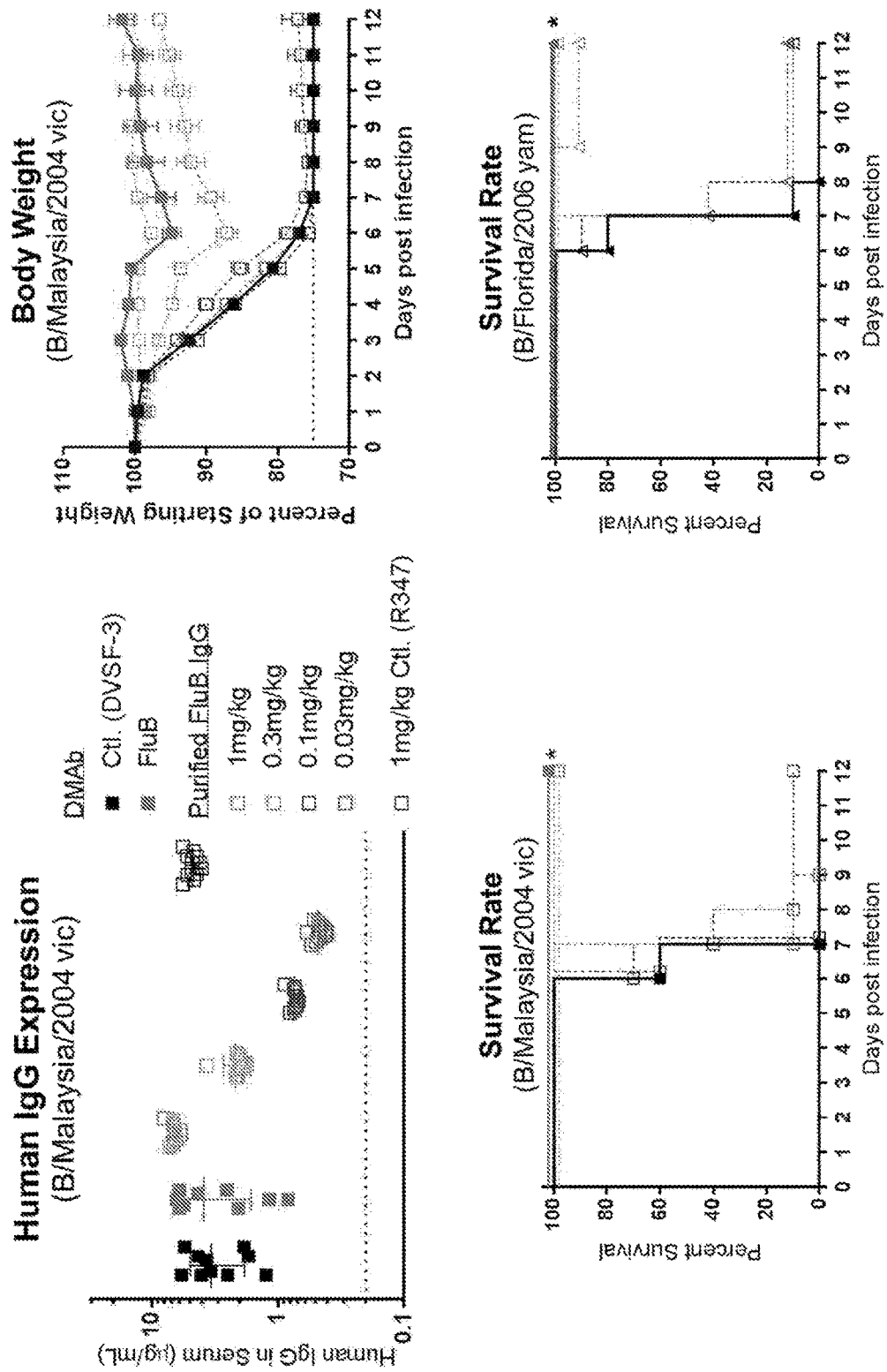
FIG. 12 depicts results of experiments demonstrating FluB DMAb protects mice from lethal influenza B infection to similar levels as purified FluB IgG at 1 mg/kg. Serum concentrations of DMAb in relation to purified IgG at time of infection. Body weight loss, and survival rate after challenge with lethal influenza B infection, * significant survival benefit of FluB DMAb compared to control DmAb $p<0.0001$ by log-rant test.
Figure 13:
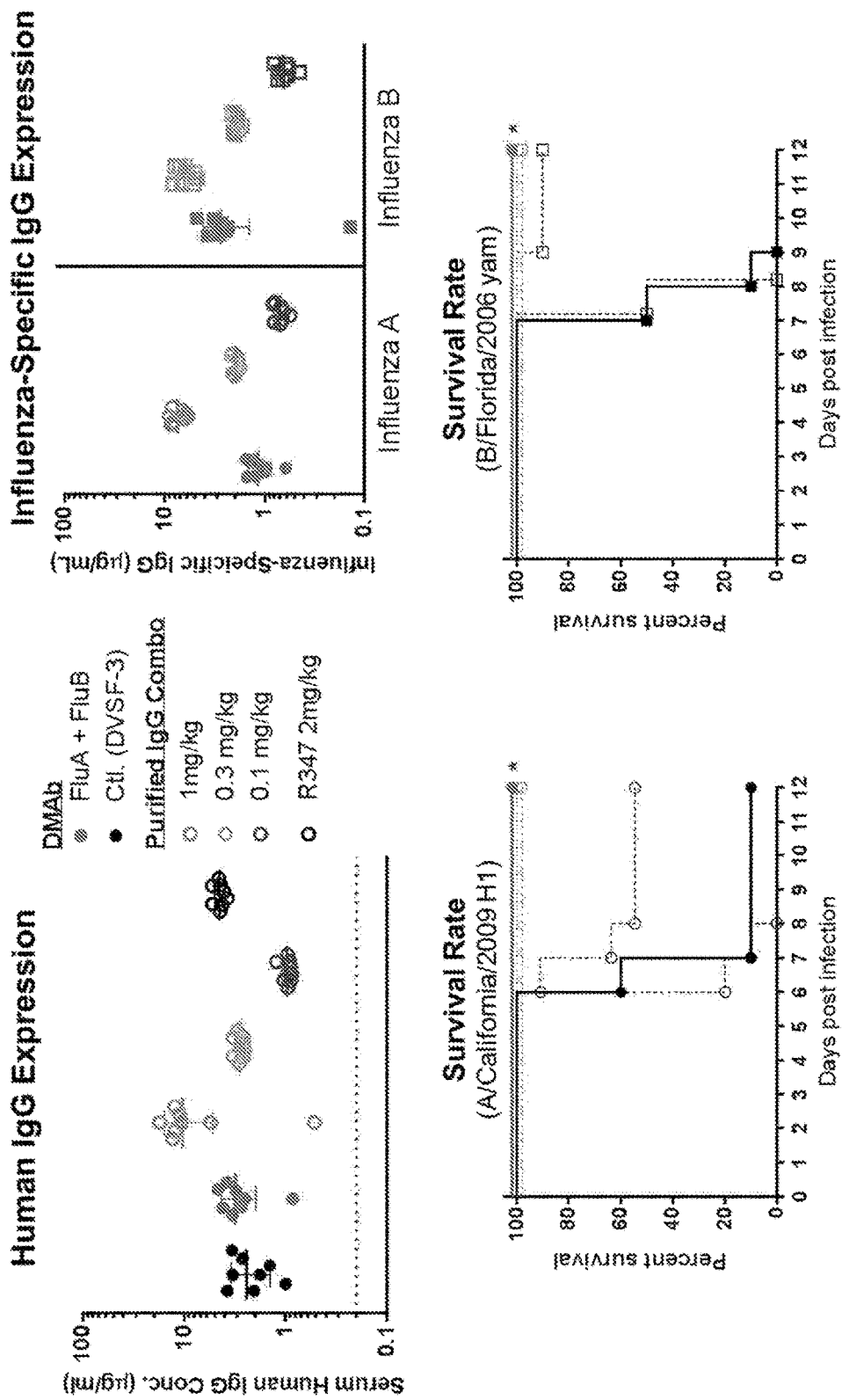
FIG. 13 depicts results of experiments demonstrating FluA and FluB DMAbs when administered in combination protects mice from either lethal influenza A or B infection. Serum concentrations of Flu DMAb combinations in relation to purified IgG combinations at time of infection. Influenza A or B specific quantitation show that Combination DMAb treatment results in similar levels of expression seen when given alone. Survival rate after challenge with lethal influenza A or B infection, * significant survival benefit of FluA+FluB DMAb compared to control DmAb $p<0.0001$ by log-rant test.
Figures 14A, 14B, 14C, 14D, 14E, 14F:
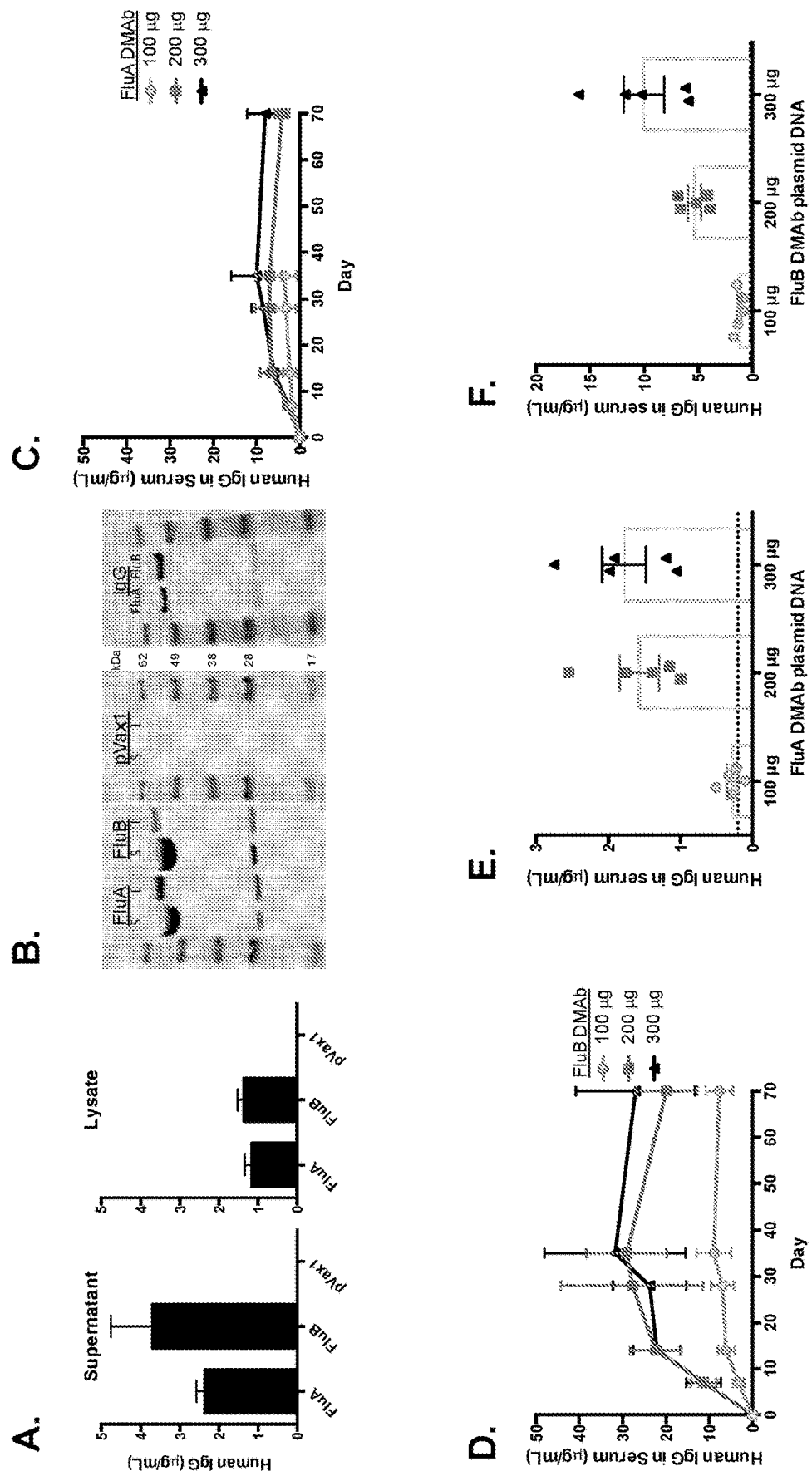
FIG. 14A through FIG. 14F, depicts results of experiments demonstrating in vitro and in vivo expression of DNA-encoded monoclonal antibody (DMAb) constructs.
Figures 15A, 15B, 15C:
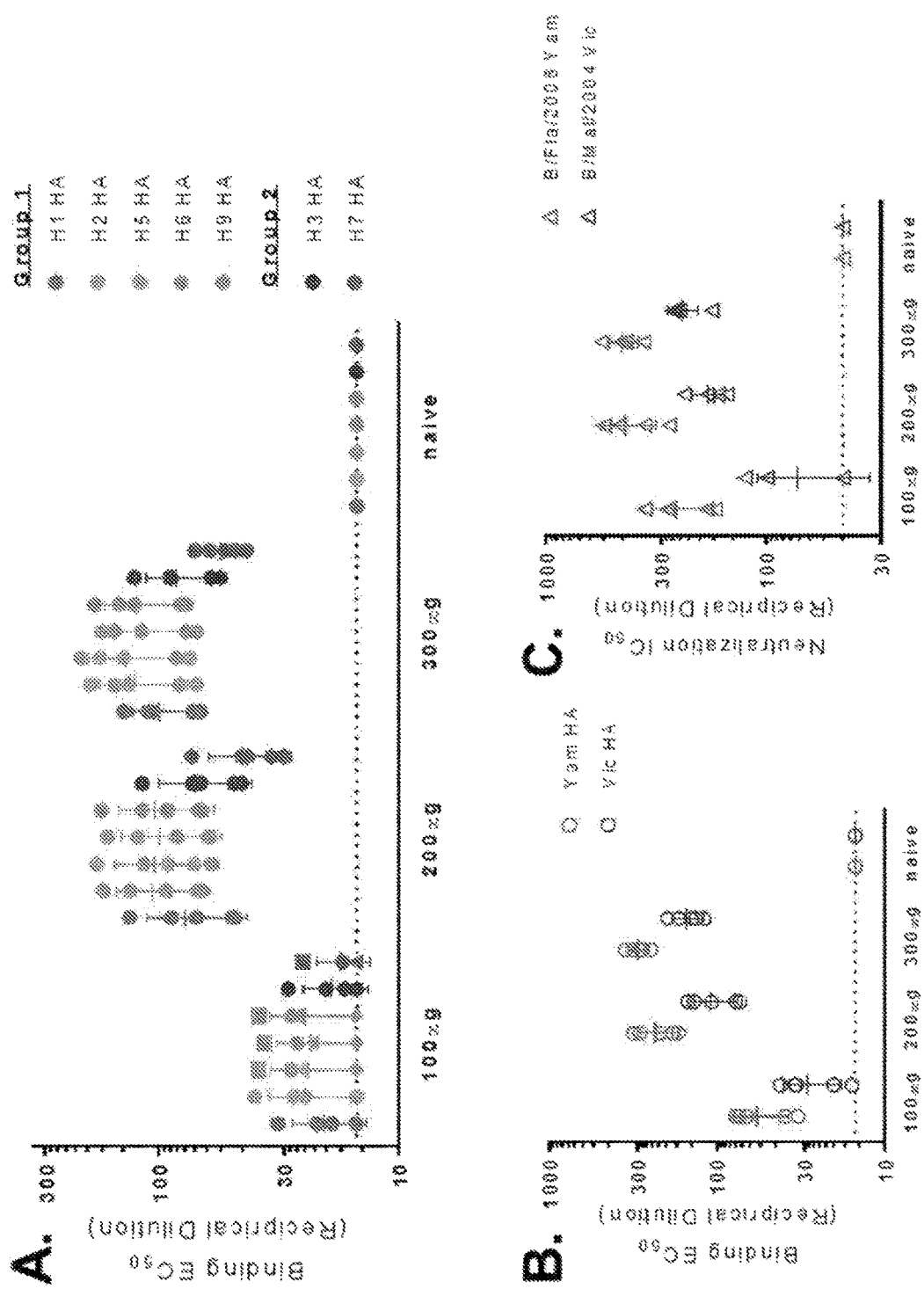
FIG. 15A through FIG. 15C, depicts results of experiments demonstrating serum FluA DMAb and FluB DMAb are functional. Functional assays performed with sera from BALB/c mice collected 5 days after treatment with 100-300 μg of FluA or FluB DMAb plasmid DNA.
Figure 16A:
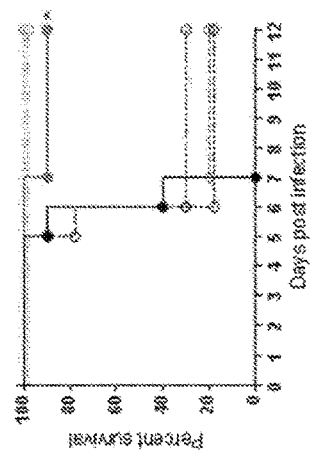
FIG. 16A through FIG. 16F, depicts results of experiments demonstrating FluA DMAb protects mice from diverse lethal influenza A challenges. BALB/c mice were treated with FluA DMAb plasmid DNA (closed symbols) 4-5 days prior to intranasal infection with A/California/7/2009 H1N1 (A-C) or re-assorted rA/HongKong/8/68×PR8 H3N1 (D-F). One day prior to infection, separate mice received 0.03-1 mg/kg FluA protein monoclonal antibody i.p. (open symbols). Mice treated with 300 μg irrelevant DMAb (DVSF-3) or 1 mg/kg non-specific protein monoclonal antibody (R347) served as controls.
Figure 16B:
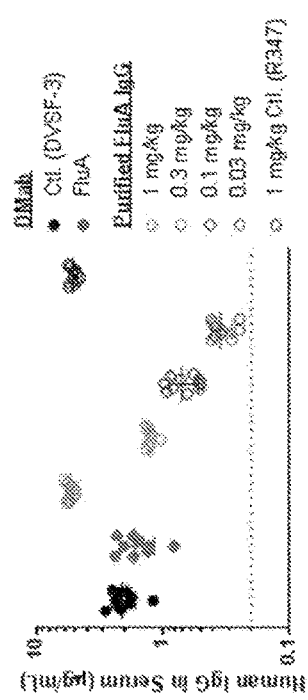
Figure 16C:
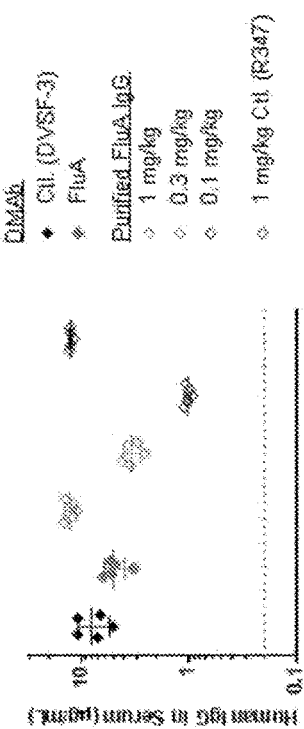
Figure 16D:
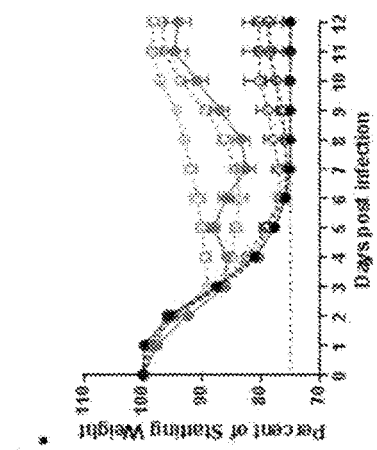
Figure 16E:
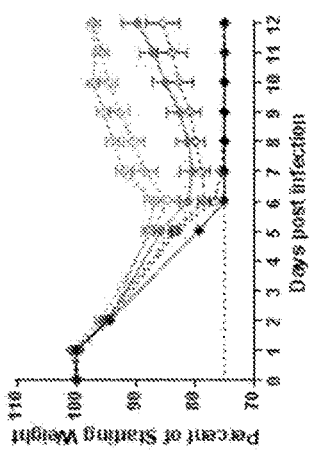
Figure 16F:
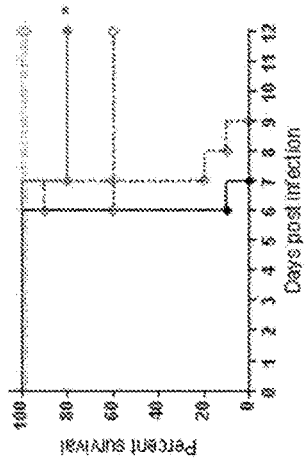

The experiments presented herein demonstrate that anti-HA 5J8 and anti-HA FI6 DNA Monoclonal Antibodies (DMAb) are expressed in vivo at high levels in mouse serum following intramuscular electroporation of plasmid DNA constructs expressing codon-optimized antibody variable sequences. Antibodies produced from muscle cells in vivo are functional and binding in vitro. DMAb provide a safe, economical, practical alternative to purified protein monoclonal antibody therapies targeting influenza HA.

DMAb have several advantages over purified protein mAb and viral-vectors. With respect to protein mAb, DMAb is relatively inexpensive to manufacture; thermally stable; easy to distribute; modifiable; and induces persistent expression without need for frequent re-administration. With respect to viral vectors, DMAb is safe and non-integrating; non-immunogenic; can be delivered repeatedly; no pre-existing serology; and induces acute expression for rapid administration. Potent & persistent expression of DMAb provides a substantial benefit in treatment of chronic conditions with potential need for re-dosing, such as cancer and auto-immune disease. Inexpensive DNA vector production & distribution provides enhanced affordability, especially in the developing world and where there is chronic need. It is understood that the foregoing detailed description and accompanying examples are merely illustrative and are not to be taken as limitations upon the scope of the invention, which is defined solely by the appended claims and their equivalents.

Example 2

The studies presented herein demonstrate the current development of an alternative passive vaccine approach that delivers full-length human broadly neutralizing antibodies against influenza A and B viruses via electroporation of synthetic plasmid DNA (DMAb) in vivo.

The methods and materials are now described.

Anti-influenza A or B specific human antibody sequences were genetically optimized and cloned into plasmid pGX001. Each candidate was injected intramuscularly followed by electroporation (IM-EP) in BALB/c mice. In vivo antibody expression was monitored and functional activity was confirmed by HA binding and virus neutralization. At various times post IM-EP, mice were challenged with lethal doses of H1 or H3 influenza A subtypes or influenza B viruses originating from both lineages, respectively. Infected animals were monitored for survival and body weight loss IgG Quantification and HA Protein Binding The amount of human IgG in mouse serum was determined by ELISA. HA binding ELISA preformed on purified recombinant trimeric HAs proteins from various influenza A subtypes and influenza B lineages.

Microneutralization Assay

Neutralization activity was measured against a panel of influenza viruses using MDCK cells and measuring neuraminidase activity similar as described in Kallewaard et al, 2016.

In Vivo Efficacy

Balb/c mice were given an intramuscular injection of DMAb plasmid/s followed immediately by electroporation using a CELLECTRA 3P adaptive constant current device (Inovio Pharmaceuticals). Mice were challenged with a lethal dose of influenza A (A/California/7/2009 3×$LD_{50}$, 7:1 A/Puerto Rico/8/34:A/Hong Kong/8/68 7×$LD_{50}$) four days later or for influenza B (B/Malaysia/2506/2004 10×$LD_{50}$, B/Florida/4/2006 7×$LD_{50}$) five days later. For comparison to IgG, groups of mice were given graded concentrations of purified mAb by IP injection one day before challenge. Serum samples were collected on the day of infection. Bodyweight loss and survival was monitored for 12 days post infection. Mice were euthanized at 25% loss of original bodyweight.

Animal studies were approved and conducted in accordance with the guidelines set by the Animal Care and Use Review Office of the U.S. Army Medical Department, and by MedImmune and University of Pennsylvania's Institutional Animal Care and Use Committees The results of the experiments are now described In Vivo Produced DNA-Encoded Antibodies (DMAbs) Express Functional FluA and FluB mAbs Quantification of DMAbs (FIG. 8) in serum confirm IgG expression and indicate the protein is functional. Serum was collected day 5 (FIG. 9) post electroporation of FluA DMAb and FluB DMAb and evaluated for human IgG expression, binding activity to a variety of HA proteins and neutralization activity. Serum antibody from both FluA-DMAb and FluB-DMAb-treated animals exhibited HA binding and virus neutralization activity similar to that of in vitro produced mAbs at comparable IgG concentrations, indicating that the muscle cell produced DMAb's were expressed and functional in vivo (FIG. 10).

DMAbs Engineered from Anti-Influenza A and B mAbs Protect from Lethal Influenza Infection to a Similar Extent as Purified IgG mAbs In influenza A challenge studies, administration of FluA-DMAb significantly protected mice from lethal virus infection compared to an irrelevant control DMAb, and reduced bodyweight loss. FluA DMAb protects mice from lethal influenza A infection to similar levels as purified FluA IgG at 0.3 mg/kg (FIG. 11) Similarly, when mice were given FluB-DMAb followed by lethal influenza B infection, the FluB-DMAb resulted in 100% survival against lethal infection with influenza B viruses from either lineage. Similarly, FluB DMAb protects mice from lethal influenza B infection to similar levels as purified FluB IgG at 1 mg/kg (FIG. 12). FluA and FluB DMAb Combination Therapy Results in Protection from Either Influenza A or B Challenge When FluA and FluB DMAbs are administered in combination, they provide protection from both influenza A and B infection. Combined administration of FluA DMAb and FluB DMAb produced Influenza A IgG and Influenza B IgG serum expression. Animals were protected from either influenza A or B lethal infection (FIG. 13).

Taken together, these studies demonstrate that DMAbs engineered from broadly neutralizing anti-influenza mAbs express fully functional antibodies in vivo at sufficient levels to prevent lethal murine infection of influenza A and B viruses. These results suggest that synthetic DNA delivery of full-length IgG mAbs may be a feasible platform strategy for universal influenza immunoprophylaxis, and could be adapted to other infectious pathogens in which cross-reactive mAbs have been characterized.

Example 3

The studies presented herein demonstrate the generation of synthetic plasmid DNA encoding two novel and broadly cross-protective monoclonal antibodies. In vivo electroporation of plasmid DNA-encoded monoclonal antibody (DMAb) constructs generated robust levels of functional antibodies directed against influenza A and B in mouse sera. Animals treated with the influenza A DMAb survived lethal Group 1 and Group 2 influenza A challenges, and those treated with the influenza B DMAb were protected against lethal Victoria and Yamagata lineage influenza B morbidity and mortality. Furthering the universal cross-protective potential of this technology, when the two DMAbs were co-administered, animals were successfully protected against severe influenza A and B infections. In addition, the delivery of anti-influenza DMAbs yielded immediate protection against influenza challenge but did not inhibit protective host immunity against influenza. DMAb produced in vivo and protein monoclonal antibody delivered intraperitoneally conferred similar protection against lethal influenza challenges, presenting DMAb as a practical alternative for immunoprophylaxis against severe influenza infection.

The methods and materials are now described.

DNA-Encoded Monoclonal Antibody Constructs

Monoclonal antibodies were isolated using similar methodology as described previously (Kallewaard et al., 2016, 166:596-608; Pappas et al., 2014, Nature 516:418-22; Traggiai et al., 2004, Nat Med 10:871-5). The cross reactive influenza A monoclonal antibody (FluA) was isolated based on cross-reactive binding to H5 and H7 HA proteins (Kallewaard et al., 2016, 166:596-608) and the influenza B monoclonal antibody (FluB) was isolated based on neutralization activity against distinct lineages of influenza B. Variable gene sequences were isolated from cross-reactive clones by RT-PCR, cloned, and further modified to revert nonessential non-germline framework amino acid changes. Full-length human IgG1κ were transiently expressed in CHO cells and purified for use in in vivo studies. Plasmid DNA-encoded monoclonal antibody (DMAb) constructs were engineered as previously described (Muthumani et al., 2016, J Infect Dis 214:369-78; Flingai et al., 2015, Sci Rep 5:12616). DMAb constructs encoded fully human IgG1κ monoclonal antibodies FluA DMAb and FluB DMAb. Antibody amino acid sequences were DNA codon-optimized and RNA-optimized for expression in human/mouse, and resulting DNA transgenes were synthesized de novo (Genscript, Picastaway, NJ, USA). Synthetic transgenes were restriction-cloned into a modified pVax1 mammalian expression vector (Invitrogen) under the cytomegalovirus (CMV) immediate-early promoter. IgE heavy- and light-chain leader sequences were added for cellular processing and secretion. In initial studies (FIG. 14 through FIG. 17), transgenes consisted of antibody heavy- and light-chain sequences separated by a furin/picornavirus-2A (P2A) peptide cleavage site sequence, yielding expression of heavy- and light-chain peptides from a single plasmid in cis. In later studies with co-administration of FluA and FluB DMAb (FIG. 18), two FluA DMAb constructs individually expressing heavy-chain or light-chain FluA peptides were mixed for expression of heavy- and light-chain FluA peptides from separate plasmids in trans.

Transfection & Western Blot

Human 293T cells (ATCC) were maintained in Dulbeco's Modified Eagle Medium (Invitrogen) supplemented with 10% fetal bovine serum. One day prior to transfection, cells were plated $0.25\times10^6$ cells per well in a 12-well plate and transfected with 0.5 μg plasmid DNA using GeneJammer (Agilent Technologies). Forty-eight hours later, supernatants were collected and adherent cells were lysed with 1× Cell Lysis Buffer (Cell Signaling) with protease inhibitor cocktail (Roche Boehringer Mannheim). Approximately 50 μg of total supernatant/lysate protein and 10 μg of protein IgG were run with SeeBlue Plus2 pre-stained protein standard (Thermo Fisher Scientific) on precast 4-12% Bis-tris gels (Invitrogen) and transferred to an Immohilon-FL PVDF membrane (EMD Millipore) using the iBlot 2 Dry Blotting System (Thermo Fisher Scientific). Heavy- and light-chain peptides were identified using IRDye 800CW goat anti-human IgG (H+L) (LI-COR Biosciences) (1:10,000). Fluorescent blots were scanned with the Odyssey CLx (LI-COR Biosciences).

Quantitative ELISA

For quantification of total human IgG1λ in cell lysates, cell supernatants, and mouse sera in FIG. 14 and FIG. 19, 96-well MaxiSorp plates (Nunc) were coated overnight at 4° C. with 10 μg/mL goat anti-human IgG $F_c$ fragment (Bethyl Laboratories). Plates were blocked with 10% FBS in PBS. Sample was diluted in 1×PBS+0.1% $Tween_{20}$ (PBST) and added to plates for 1 hour. A standard curve was generated using purified human IgG1κ (Bethyl Laboratories). Plates were stained with HRP-conjugated secondary antibody goat anti-human kappa light-chain (Bethyl Laboratories) (1:20,000) for 1 hour, developed using SigmaFast OPD (Sigma-Aldrich), and stopped with 2 N sulfuric acid. Absorbance 450 nm was measured on a Synergy2 plate reader (Biotek).

Quantitation of human IgG in murine challenge studies was performed using 384-well black MaxiSorp plates (Nalgene Nunc) coated overnight at 4° C. with 10 μg/mL goat anti-Human IgG (H+L) (Pierce). Plates were blocked with Casein Blocker (Thermo), and serum samples and a standard curve (10 μg/mL of ChromPure Human IgG, whole molecule) (Jackson Labs) were serially diluted. Plates were washed and stained with a donkey anti-Human IgG-HRP secondary antibody (Jackson) (1:4,000) and visualized using SuperSignal ELISA Pico Reagent (Thermo). Luminescence was measured using Perkin Elmer Envision.

Quantification of specific influenza A or B human IgG in the sera of mice was performed as described above, with 3 μg/mL of HA protein from A/Vietnam/1203/2004 (H5N1) or 3 μg/mL of HA from B/Florida/4/2006 (Yamagata) as coating reagent. FluA or FluB purified protein IgG were used as standards for the influenza A and B assays respectively.

Binding ELISA

Recombinant hemagglutinin (HA) proteins were expressed and purified as previously described (Benjamin et al., 2014, J Virol 88:6743-50). ELISA binding assays were performed using 384 well MaxiSorp plates (Nunc) coated with 5 µg/ml of purified HA protein from A/Perth/16/2009 (H3N2), A/Hong Kong/G9/1997 (H9N2), and B/Brisbane/60/2008 (Victoria); or 3 µg/ml of purified HA protein from A/California/07/2009 (H1N1), A/Vietnam/1203/2004 (H5N1), A/Netherlands/2003 (H7N7), A/Missouri/2006 (H2N3), and B/Florida/4/2006 (Yamagata). ELISA plates were blocked with Casein (Thermo Scientific) and serially diluted antibodies were incubated for one hour at room temperature. Bound antibodies were detected using a peroxidase-conjugated mouse anti-human IgG antibody (KPL) (1:10,000), followed by development with TMB solution (KPL), and absorbance measurement at an OD of 450 nm. Mouse serum reactivity to HA was preformed as described above with the exception of secondary antibody of peroxidase-conjugated goat anti-mouse IgG antibody (DAKO) (1:5,000).

Viral Stocks, in vitro Neutralization & Hemmaglutination Inhibition

Wild-type influenza strains were obtained from the Centers for Disease Control and Prevention, or purchased from the American Tissue Culture Collection. A re-assortant H3 virus produced by reverse genetics (rA/HK/68) contained the H3 HA from A/Hong Kong/8/68 (H3N2) and the remaining 7 gene segments from A/Puerto Rico/8/34 (H1N1); the HA of this virus also contained a N165S mutation that enhances murine pathogenesis (Jin et al., 2003, Virology 306:18-24). All viruses were propagated in embryonated chicken eggs, and virus titers were determined by mean 50% tissue culture infective dose ($TCID_{50}$) per milliliter. The microneutralization assay was performed as previously described (Benjamin et al., 2014, J Virol 88:6743-50). Briefly, 60 $TCID_{50}$ of virus/well was added to three-fold serial dilutions of serum or purified FluB antibody diluted in naïve serum in a 384-well plate in complete MEM medium containing 0.75 µg/ml N-tosyl-L-phenylalanyl chloromethyl keytone (TPCK) Trypsin (Worthington) in duplicate wells. After one-hour incubation at 33° C. and 5% $CO_2$, $2 \times 10^4$ Madin-Darby Canine Kidney (MDCK) cells/well were added to the plate. Plates were incubated at 33° C. and 5% $CO_2$ for approximately 40 hours, and neuraminidase (NA) activity was measured by adding a fluorescently-labeled substrate methylumbelliferyl-N-acetyl neuraminic acid (MU-NANA) (Sigma) to each well at 37° C. for 1 hour. Virus replication represented by NA activity was quantified by reading fluorescence using the following settings: excitation 355 nm, emission 460 nm, 10 flashes per well. Hemagglutination inhibition assay was performed with serum collected on Day 21 post-infection as previously described.

Intramuscular DNA Electroporation

Thirty minutes prior to DNA electroporation, female BALB/C and CAnN.Cg-Foxn1$^{nu}$/Crl mice (Charles River) were pre-treated at each delivery site with an intramuscular (i.m.) injection of 12 Units (30 µL) hyaluronidase enzyme (Sigma-Aldrich). In initial studies (FIG. 14 through FIG. 17), 100 µg (30 µL) of either FluA or FluB DMAb plasmid was injected i.m. to the tibialis anterior (TA) and/or quadriceps (Q) muscle; mice received 100 µg DNA at one site (TA), 200 µg DNA at two sites (right TA+left TA), or 300 µg DNA at three sites (right TA+left TA+Q). In later co-administration studies (FIG. 18), mice received both FluA and FluB DMAb constructs. The FluA construct design was modified to express heavy-chain and light-chain peptides on separate plasmids, generating equivalent serum levels of FluA IgG from fewer injection sites than the one-plasmid design. In this case, 100 µg of a 1:1 (wt:wt) mixture of FluA heavy-chain and light-chain plasmid was delivered over two sites (right TA+right Q), and 200 µg plasmid FluB was delivered over two sites as before (left TA+left Q). Intramuscular electroporation (IM-EP) was performed immediately after each DNA injection with a CELLECTRA 3P adaptive constant current device (Inovio Pharmaceuticals).

Lethal Influenza Challenge

Six- to eight-week-old BALB/c mice (Harlan Laboratories) received FluA DMAb, FluB DMAb, or an irrelevant control DMAb (DVSF-3, previously described (Flingai et al., 2015, Sci Rep 5:12616)) via IM-EP 4-5 days prior to infection. One day prior to infection, protein IgG monoclonal antibody with amino acid sequence identical to that encoded by plasmid DMAb was administered to separate groups of mice intraperitoneally (i.p.) at doses ranging from 0.03 mg/kg to 1.0 mg/kg. Control mice received non-specific protein IgG R347 i.p. Mice received intranasal infection with $3 \times LD_{50}$ of A/California/07/2009 (H1N1) ($9.5 \times 10^4$ $TCID_{50}$/mouse), $7 \times LD_{50}$ of rA/HK/68 (H3) ($1.2 \times 10^5$ $TCID_{50}$/mouse), $10 \times LD_{50}$ B/Malaysia/2506/2004 (Victoria) ($3.6 \times 10^4$ $TCID_{50}$/mouse), or $7 \times LD_{50}$ B/Florida/4/2006 (Yamagata) ($7.0 \times 10^4$ $TCID_{50}$/mouse). All mice were monitored daily for weight loss and survival for 12 days (mice with body weight loss ≥25% were euthanized). Blood was collected on the day of infection to assess the amount of human IgG in the serum. To assess viral load in the lungs, additional mice were euthanized five days post-infection. Whole lungs were homogenized in 10% (wt/vol) sterile L15 medium (Invitrogen) and titrated on MDCK cells to determine the $TCID_{50}$/gram of tissue. In homologous re-infection studies, blood samples were taken from all surviving mice 21 days after initial infection to confirm clearance and absence of human IgG. Twenty-eight days after the initial infection, mice were re-challenged with a virus strain and lethal dose identical to the initial infection.

All animal housing and experimentation were approved by and conducted in accordance with the guidelines set by the NIH, the Animal Care and Use Review Office of the U.S. Army Medical Department, the University of Pennsylvania Perelman School of Medicine Institutional Animal Care and Use Committee, and MedImmune Institutional Animal Care and Use Committee. All murine challenge studies were conducted in accordance with and subsequently performed in an Association for the Assessment and Accreditation of Laboratory Animal Care (AAALAC)-certified facility.

Analyses & Statistics

Standard curves and graphs were prepared using GraphPad Prism 6. $EC_{50}$ and $IC_{50}$ values were calculated using a non-linear regression of log (reciprocal serum dilution) vs response. Survival data were expressed using Kaplan-Meier survival curves with p-values calculated by log-rank (Mantel-Cox) test.

The results of the experiments are now described.

Figures 17A, 17B, 17C, 17D, 17E, 17F:
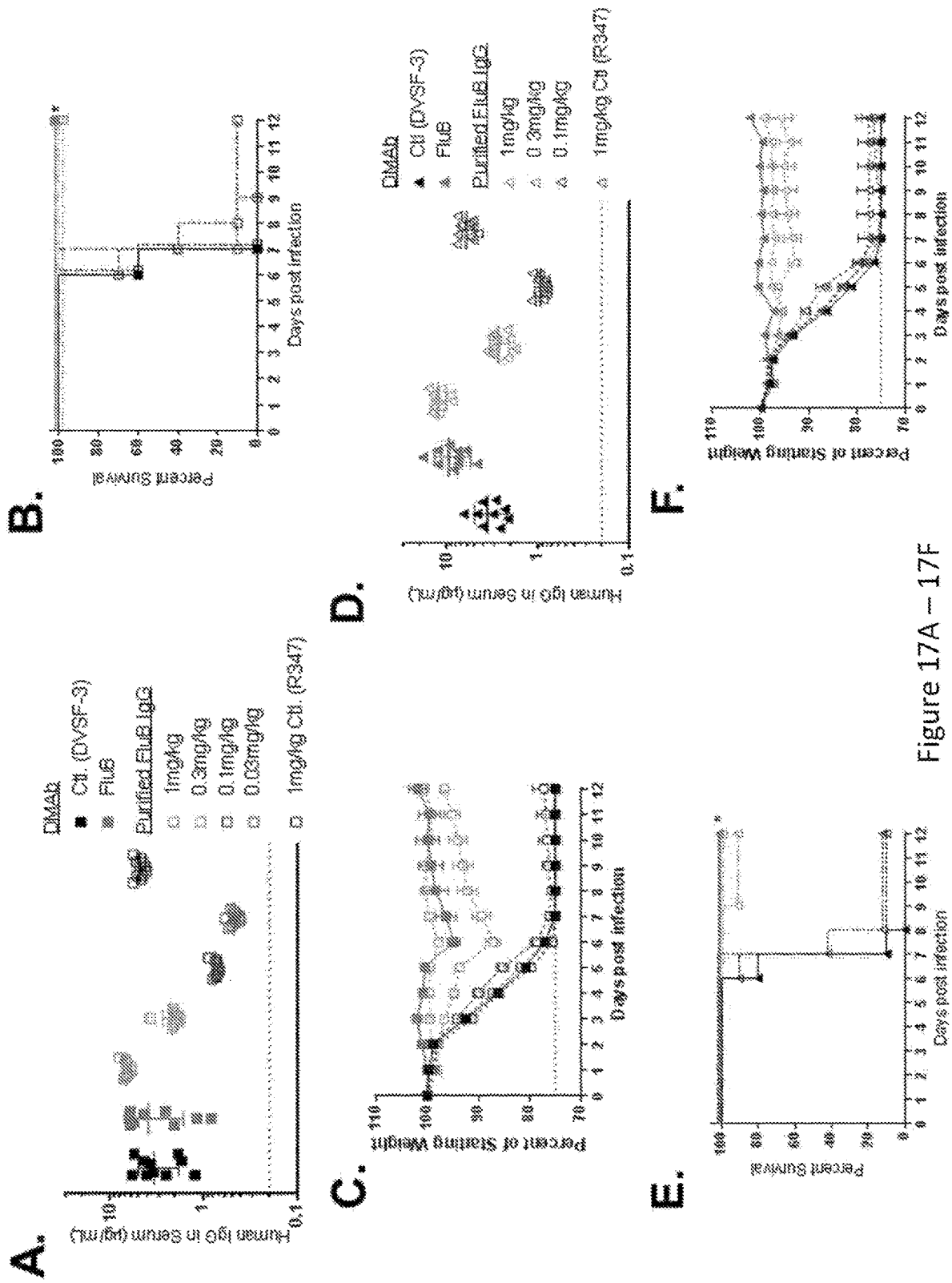
FIG. 17A through FIG. 17F, depicts results of experiments demonstrating FluB DMAb protects mice from diverse lethal influenza B challenges. BALB/c mice were treated with FluB DMAb plasmid DNA 5 days prior to infection with B/Malaysia/2506/2004 Victoria (A-C) or B/Florida/4/2006 Yamagata (D-F) lineage virus. One day prior to infection, separate groups of mice received 0.03-1 mg/kg FluB protein monoclonal antibody i.p.
Figure 19:
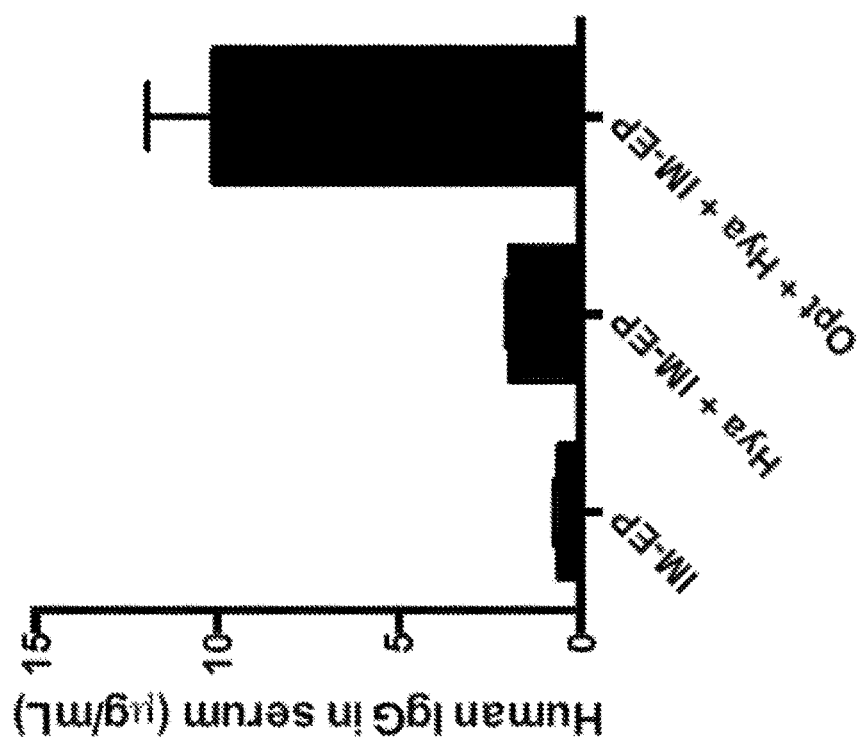

DNA-Encoded Monoclonal Antibodies (DMAb) Against Influenza Viruses are Expressed In Vitro and In Vivo Broadly-neutralizing monoclonal antibodies against influenza A (FluA) and influenza B (FluB) were isolated from human memory B-cells as previously described (Pappas et al., 2014, Nature, 516: 418-22; Traggiai et al., 2004, Nat Med, 10: 871-875). The FluA monoclonal antibody is closely related to a recently published broadly-neutralizing monoclonal antibody which shows a wide range of HA cross-reactivity due to the binding to the HA stalk and is capable of neutralizing influenza A viruses from both group 1 and group 2 (average IC$_{50}$ of 2.56 µg/ml, data not shown) (Kallewaard et al., 2016, Cell, 6743-50). The FluB monoclonal antibody was identified and selected based on its ability to potently neutralize influenza B viruses belonging to both Victoria and Yamagata lineages (average IC$_{50}$ of 0.64 µg/ml, data not shown). This antibody binds to a conserved region in the globular head of influenza B HA, and can inhibit viral hemagglutination of red blood cells. To test the utility of DMAb delivery to prevent severe influenza infection, a synthetic DNA transgene encoding either human IgG FluA or FluB was synthesized de novo, and cloned into a mammalian expression plasmid. Multiple modifications were made to enhance DMAb expression including DNA codon optimization, RNA optimization, and formulation of plasmid DNA (FIG. 19) (Muthumani et al., 2016, J Infect Dis 214:369-78; Flingai et al., 2015, Sci Rep 5:12616). Quantitative ELISA of human IgG in lysates and supernatants of human embryonic kidney 293T cells transfected with DMAb constructs confirmed intracellular expression and extracellular secretion of assembled FluA and FluB antibodies (FIG. 14A). Human IgG Western blot also demonstrated antibody heavy-chain and light-chain were present in transfected 293T cell supernatants and lysates (FIG. 14B).

FluA or FluB DMAb plasmid DNA was administered to athymic CAnN.Cg-Foxn1$^{nu}$/Crl nude mice by intramuscular injection at doses from 100 μg to 300 μg, utilizing intramuscular electroporation (IM-EP) formulated with hyaluronidase to enhance DMAb delivery and expression (FIG. 19). Peak expression levels in nude mouse sera reached a mean of 10.0 μg/mL (±2.6 SEM) and 31.8 μg/mL (±8.1 SEM) for FluA DMAb and FluB DMAb respectively, with significant human IgG expression observed 10 weeks after DMAb delivery (FIGS. 14C and 14D) and beyond.

Next, the expression of anti-influenza DMAb was defined in immune-competent BALB/c mice (FIGS. 14E and 14F), an established influenza challenge model. BALB/c mice received 100 μg to 300 μg of plasmid DNA via IM-EP. The FluA DMAb construct generated modest levels of human IgG in BALB/c mouse sera as measured five days post-delivery (300 μg plasmid mean 1.8 μg/mL±0.3 SEM). Similar to what was observed in nude mice, FluB DMAb expression was more robust than FluA DMAb expression five days post-delivery (200 μg mean 5.4 μg/mL±0.6 SEM, 300 μg mean 10 μg/mL±1.9 SEM). Unlike the stable expression observed in nude mice, serum DMAb levels in BALB/c mice were undetectable 10 days post-delivery, likely due to mouse adaptive anti-human-IgG responses against the expressed DMAb. Collectively, these data clearly demonstrated DMAb human IgG was produced at substantial levels in vivo following administration of plasmid constructs.

In Vivo-Expressed Influenza DMAbs are Functionally Active and Demonstrate Broad Cross-Reactivity To test the functionality of the DMAb generated in vivo, sera collected from DMAb-treated BALB/c mice were tested for in vitro binding activity. FluA DMAb from sera bound to a comprehensive array of influenza A Group 1 and Group 2 HA antigens, from viruses known to infect humans, including recombinant trimeric HA from seasonal (H1, H3) and potentially pandemic (H2, H5, H6, H7, H9) influenza isolates (FIG. 15A), as well as recombinant monomeric HA H10 (FIG. 20). FluB DMAb in murine sera bound to influenza B HA from both Victoria and Yamagata lineage viruses (FIG. 15B). Half-maximal effective concentrations ($EC_{50}$) of reciprocal serum dilutions reflect the higher binding activity in sera of mice treated with 300 μg versus 100 μg plasmid DNA, reflecting increased DMAb expression in animals receiving more plasmid DNA.

The potent in vitro neutralization capabilities of the parent FluB monoclonal antibody allowed for neutralization activity testing whereas the potency of the FluA monoclonal antibody did not allow for differentiation from the non-specific interference of mouse serum in the microneutralization assay. Sera from mice that received FluB DMAb plasmid constructs effectively neutralized both Yamagata and Victoria lineage influenza B viruses in an in vitro cell-based assay (FIG. 15C), with a similar pattern of reactivity as seen in binding assays. After normalizing for human IgG concentration in each sample, the calculated half maximal inhibitory concentration ($IC_{50}$) from mice treated with FluB DMAb plasmid (0.015 μg/mL for B/Florida/4/2006 and 0.030 μg/mL for B/Malaysia/2506/2004) was similar to that of purified protein FluB monoclonal antibody (0.011 μg/mL for B/Florida/4/2006 and 0.047 μg/mL for B/Malaysia/2506/2004), within the overall error of this cell-based assay. The presence of HA-binding human IgG in mice receiving FluA and FluB DMAb plasmid constructs, and the neutralization titers in mice treated with FluB DMAb plasmid constructs, confirmed in vivo expression of functional DMAb and demonstrated the remarkable broad cross-reactivity of these novel anti-influenza FluA and FluB antibodies.

Influenza DMAbs Protect Mice from Diverse Influenza A and Influenza B Lethal Challenges To evaluate the utility of the technology in vivo, DMAb treated animals were evaluated in lethal influenza challenge models. Animals were administered 300 μg FluA DMAb or an irrelevant DMAb control (DVSF-3 (Flingai et al., 2015, Sci Rep 5:12616)) via IM-EP, then challenged with a lethal dose of A/California/7/2009 H1N1 (A/CA/09 H1) four days post-electroporation (FIG. 16). For direct in vivo comparison of DMAb and protein IgG, a dilution series of FluA protein monoclonal antibody was delivered i.p. to separate groups of mice one day prior to infection. Serum samples obtained from all animals at the time of infection showed that FluA DMAb treatment resulted in similar mean human IgG concentrations and HA binding activity as observed in mice treated with 0.3 mg/kg of FluA protein IgG (FIG. 16A and FIG. 21). When challenged with a lethal dose of A/California/7/2009 H1N1 (A/CA/09 H1) virus, FluA DMAb treatment provided a 90% survival benefit whereas all animals treated with a control DMAb against dengue virus (DVSF-3) succumbed to infection (FIG. 16B). Corresponding to human IgG expression levels, the FluA DMAb treatment and 0.3 mg/kg of FluA purified protein exhibited similar protection from lethality and influenza-induced weight loss (FIG. 16C).

Expanding these results with another clinically relevant influenza A virus, a similar study was preformed using a lethal challenge of rA/Hong Kong/8/68 H3N1 (rA/HK/68 H3) given five days post-DMAb-administration. Again, at the time of infection human antibody levels showed FluA DMAb and 0.3 mg/kg of FluA protein IgG at similar concentrations (FIG. 16D). After lethal rA/HK/68 H3 challenge, FluA DMAb-treated animals had a significant survival benefit compared to DMAb controls (80% survival rate with FluA DMAb versus 0% survival rate with control DMAb) (FIG. 16E). These results show FluA DMAb prevents lethal influenza A infection by clinically relevant H1 and H3 subtypes known to cause disease in humans, and crucially demonstrate similar in vivo function of FluA antibody generated via the DMAb platform versus purified FluA antibody delivered i.p.

To further investigate the prophylactic potential of DMAb technology, similar lethal challenge studies were performed to evaluate the activity of the FluB DMAb. In these studies, mice were administered 200 μg FluB DMAb plasmid construct or control DMAb via IM-EP, then challenged with a lethal dose of virus from the Victoria (B/Malayaisa/2506/2004 (B/Mal/04)) or Yamagata lineage (B/Florida/4/2006 (B/Fla/06)) five days later (FIG. 17). Again, for direct comparison of DMAb vs purified protein, purified FluB monoclonal antibody was administered i.p. to separate groups one day prior to infection. Quantification of human IgG present in mouse serum at time of B/Mal/04 challenge showed that FluB DMAb yielded similar mean human IgG concentrations and HA binding activity as observed in animals treated with 1 mg/kg of FluB protein i.p. (FIG. 17A, and FIG. 21). Remarkably, 100% of FluB DMAb-treated mice survived both Victoria and Yamagata lethal influenza B challenge, whereas non-specific DMAb controls fully succumbed to both infections by Day 8 (FIGS. 17B and 17E). Furthermore, FluB protected mice from influenza B-related morbidity with treated animals exhibiting little-to-no weight loss (FIGS. 17C and 17F). In addition, FluB-treated mice exhibited significantly lower lung viral loads than control mice (FIG. 22). Survival, weight loss, lung viral loads, and in vitro binding activity in sera of FluB DMAb-treated mice closely paralleled the same parameters in mice receiving 1 mg/kg purified FluB protein IgG, again confirming the in vivo functional equivalence of DMAb and purified protein monoclonal antibodies.

Figures 18A, 18B, 18C, 18D, 18E, 18F:
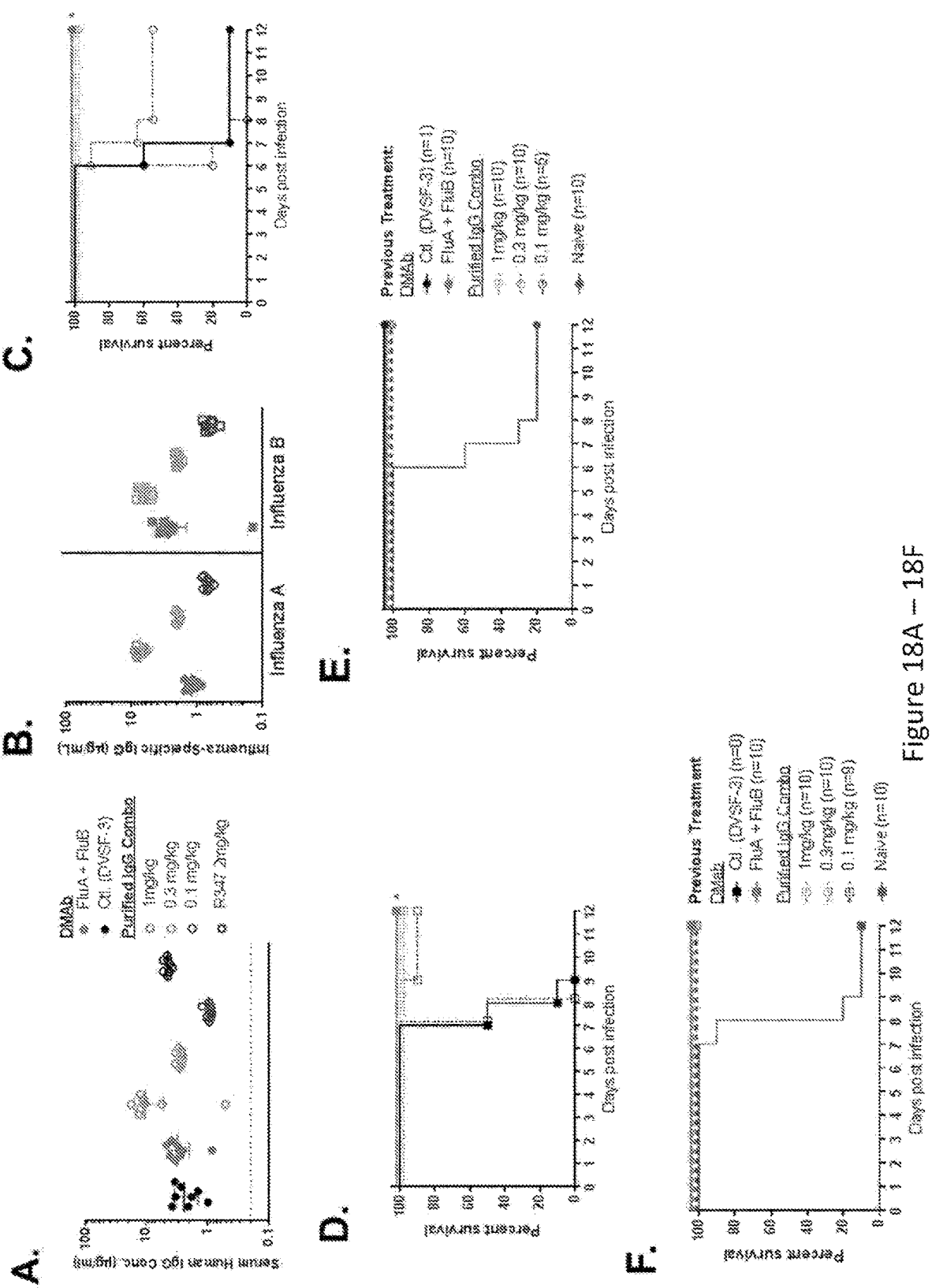
FIG. 18A through FIG. 18F, depicts results of experiments demonstrating Co-administration of FluA and FluB DMAb protects mice from lethal influenza A/B challenge and homologous re-challenge. BALB/c mice received both FluA and FluB DMAb. Separate mice were treated with both FluA plus FluB protein monoclonal antibody. Mice received initial infection with either influenza A/California/7/2009 or B/Florida/4/2006.

Co-Administration of FluA and FluB DMAb Protects Mice Against Influenza A and B Challenge, and Homologous Re-Challenge Influenza A and B viruses co-circulate, and a comprehensive immunoprophylactic strategy against seasonal infection should target both influenza types. To test the ability of the DMAb platform to serve in this role, FluA DMAb and FluB DMAb were co-administered to BALB/c mice. Five days prior to infection, mice were administered FluB DMAb, then administered FluA DMAb the following day. Comparator groups of animals received a mix of FluA and FluB purified protein monoclonal antibodies i.p. one day prior to infection. Mice were challenged with a lethal dose of either A/CA/09 H1 or B/Fla/06. Serum samples at the time of infection showed that the DMAb-treated animals had an average of 3 μg/ml of total human IgG (FIG. 18A). Influenza A- and B-specific ELISAs showed that both DMAbs exhibited expression levels similar to those observed previously (FIG. 18B), with serum levels of FluA DMAb approximating serum levels of 0.3 mg/kg FluA protein IgG delivered i.p. and FluB DMAb approximating serum levels of 1 mg/kg of FluB protein IgG delivered i.p. In challenge studies, all mice receiving FluA plus FluB DMAb were protected from lethal infection, whereas 90% and 100% of mice treated with control DMAb succumbed to the influenza A and B infections, respectively (FIGS. 18C and 18D). Again, DMAb administration and delivery of protein IgG resulted in similar levels of protection, apparent in both survival rate and body weight loss (FIG. 23).

Twenty-one days following initial infection, sera of surviving BALB/c mice had undetectable levels of human IgG (data not shown), indicating DMAb and recombinant protein were no longer present. Serum hemagglutination inhibition (HAI) and mouse anti-HA binding antibodies against the infecting influenza strain confirmed that mice mounted a host immune response to infection (FIG. 24). DMAb-treated mice were able to mount host immune responses against the virus to the same extent as the purified-IgG-treated animals.

Crucially, the presence of FluA and FluB in vivo did not prohibit protective host immune responses against challenge virus. Twenty-eight days following initial infection, all surviving mice (including one DMAb control mouse that survived initial A/CA/09 H1 infection) were re-challenged with a lethal dose of homologous influenza virus to confirm that the level of mouse host immune response was protective. All previously-challenged mice survived the lethal homologous re-challenge without substantial weight loss, whereas 80-90% of untreated age-matched mice naïve to infection did not survive (FIG. 18E, FIG. 18F, and FIG. 23). These results demonstrate protective host anti-influenza responses develop in the presence of protective levels of FluA and FluB antibodies whether expressed in vivo as DMAb or delivered as protein monoclonal antibody, demonstrating that DMAbs did not antagonize each other or the host immune response to influenza.

Discussion

Seasonal influenza infection results in an annual average of $10 billion USD in direct medical costs and $80 billion USD economic burden in the United States alone (Molinari et al., 2007, Vaccine 25:5086-96). Despite availability of influenza vaccines and anti-viral drugs, large sub-populations are susceptible to complications arising from seasonal influenza infection. Almost 90% of deaths attributed to seasonal influenza in the United States occur in adults 65 years and older (Frieden et al., 2010, MMWR 59), a population in which estimated vaccine efficacy is as low as 36% in years of significant antigenic drift. In addition to the persistent hazards of seasonal infection, pandemic influenza outbreaks threaten to outpace vaccine design. Therefore, innovative universal interventions against influenza infection are vital.

Most of the current efforts to create a universal influenza vaccine have focused on the design of recombinant antigens that can serve as immunogens to spur maturation of cross-protective anti-influenza antibodies (Yassine et al., 2015, Nat Med 21:1065-70; Impagliazzo et al., 2015, Science 349:1301-6; Bommakanti et al., 2010, PNAS 107:13701-6). Here, it was sought to bypass immunization and generate cross-protective immunity directly in vivo. Functional cross-protective anti-influenza antibodies were generated in mouse sera following intramuscular electroporation of plasmid DNA constructs encoding two HA-targeting antibodies leading to significant protection against lethal influenza A and influenza B challenges.

A plethora of protein monoclonal antibodies are commercially available for treatment of auto-immune disease, cancer, and other chronic conditions; but given the expense of administering biologics, and their limited half-life, only one protein monoclonal antibody is widely used for prophylaxis against an infectious disease target (Group, 1998, Pediatrics 102:531-7). The DMAb technology is a notable delivery alternative as DMAb produced from muscle cells in vivo and purified protein monoclonal antibodies manufactured in vitro conferred the same level of protection against lethal influenza infection in mice. Plasmid DNA lacks limitations posed by pre-existing anti-vector serology and the DMAb platform may be utilized repeatedly to deliver additional anti-influenza antibodies to combat viral escape, or antibodies aimed at entirely different pathogens (Muthumani et al., 2016, J Infect Dis 214:369-78; Flingai et al., 2015, Sci Rep 5:12616). Plasmid DNA also has little risk of genomic integration and similar plasmid designs have demonstrated safety in DNA vaccine human clinical studies.

DNA plasmid-based delivery of monoclonal antibodies is a feasible alternative to protein therapy at each step of the supply chain. In production, DMAb are inexpensive relative to protein monoclonal antibody (and viral vectors) because DNA replication does not require mammalian cell culture. In distribution, a cold-chain is unnecessary, a huge practical advantage in the developing world. DNA is simple to scale up and stable for storage, an especially important consideration in resource-limited settings. The potential for long-term DMAb expression may circumvent the need for frequent recombinant antibody injections, complementary to emerging antibody half-life extension technologies. In delivery, sustained DMAb expression may circumvent the need for frequent antibody injections whereas protein monoclonal antibodies generally display short in vivo half-lives; potent DMAb expression was observed on the order of months following DMAb delivery to nude mice. Crucially, DMAb-treated mice survived homologous re-infection indicating host immune responses to influenza infection remain intact after treatment with FluA DMAb and FluB DMAb. Conceivably, these influenza-specific DMAbs can be used to augment a vaccine campaign, generating immediate prophylaxis against severe influenza infection while allowing for an adequate vaccine-induced immune response to mature. DMAb may also provide a vital option for severely immune impaired individuals incapable of mounting antibody responses. With the ability to deliver potent functional antibody using plasmid DNA, DMAb technology provides an exceptionally broad platform of therapeutic potential.

Example 4

Presented herein are the peptide nucleic acid sequence identifiers.

| SEQ ID | Identifier |
|---|---|
| SEQ ID NO: 1 | pGX9211 amino acid |
| SEQ ID NO: 2 | pGX9212 amino acid |
| SEQ ID NO: 3 | pGX222hc amino acid |
| SEQ ID NO: 4 | pGX222lc amino acid |
| SEQ ID NO: 5 | pGX9223 amino acid |
| SEQ ID NO: 6 | pGX9231 amino acid |
| SEQ ID NO: 7 | pGX9310 amino acid |
| SEQ ID NO: 8 | pGX9311 amino acid |
| SEQ ID NO: 9 | pGX9211 nucleotide |
| SEQ ID NO: 10 | pGX9212 nucleotide |
| SEQ ID NO: 11 | pGX222hc nucleotide |
| SEQ ID NO: 12 | pGX222lc nucleotide |
| SEQ ID NO: 13 | pGX9223 nucleotide |
| SEQ ID NO: 14 | pGX9231 nucleotide |
| SEQ ID NO: 15 | pGX9310 nucleotide |
| SEQ ID NO: 16 | pGX9311 nucleotide |

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding one or more synthetic antibodies, wherein the nucleic acid molecule comprises at least one selected from the group consisting of
    a) a nucleotide sequence encoding an anti-influenza hemagglutinin (HA) synthetic antibody; and
    b) a nucleotide sequence encoding a fragment of an anti-influenza-HA synthetic antibody;
wherein the anti-influenza HA synthetic antibody comprises an amino acid sequence selected from the group consisting of a sequence at least 90% identical to SEQ ID NOs:1-8, and a functional fragment thereof.

2. The nucleic acid molecule of claim 1, wherein the anti-influenza HA synthetic antibody is selected from the group consisting of an antibody that binds to the globular head of influenza HA and an antibody that binds to the fusion subdomain of influenza HA.

3. The nucleic acid molecule of claim 1, wherein nucleic acid molecule encodes an anti-influenza HA synthetic antibody comprising an amino acid sequence selected from a sequence at least 95% identical to SEQ ID NOs:1-8, and a fragment thereof.

4. The nucleic acid molecule of claim 3, wherein the nucleic acid molecule comprises a nucleotide sequence selected from a sequence at least 90% identical to SEQ ID NOs: 9-16 and a fragment thereof.

5. The nucleic acid molecule of claim 1, comprising at least one nucleotide sequence selected from the group consisting of a first nucleotide sequence encoding a first anti-influenza-HA antibody; and a second nucleotide sequence encoding a second anti-influenza-HA antibody.

6. The nucleic acid molecule of claim 1, further comprising a nucleotide sequence encoding a cleavage domain.

7. The nucleic acid molecule of claim 1, comprising a nucleotide sequence encoding a variable heavy chain region and a variable light chain region of a anti-influenza-HA antibody.

8. The nucleic acid molecule of claim 1, comprising a nucleotide sequence encoding a constant heavy chain region and a constant light chain region of human IgG1κ.

9. The nucleic acid molecule of claim 1, comprising a nucleotide sequence encoding a polypeptide comprising a variable heavy chain region of anti-influenza-HA; a constant heavy chain region of human IgG1κ; a cleavage domain; a variable light chain region of anti-influenza-HA; and a constant light chain region of IgG1κ.

10. The nucleic acid molecule of claim 1, wherein the nucleotide sequence encodes a leader sequence.

11. The nucleic acid molecule of claim 1, wherein the nucleic acid molecule comprises an expression vector.

12. A composition comprising the nucleic acid molecule of claim 1.

13. The composition of claim 12, further comprising a pharmaceutically acceptable excipient.

14. A method of treating an influenza infection in a subject, the method comprising administering to the subject the nucleic acid molecule of claim 1.

15. The method of claim 14, wherein the influenza infection is selected from an influenza A infection and an influenza B infection.

16. A method of treating an influenza infection in a subject, the method comprising administering to the subject a composition of claim 12.

* * * * *